United States Patent [19]

Fischli et al.

[11] 4,281,188
[45] Jul. 28, 1981

[54] N'[3-(HALOBENZOYL)-4-(GLYCYLAMINO)-PHENYL]UREAS

[75] Inventors: Albert E. Fischli; Andre Szente, both of Riehen, Switzerland

[73] Assignee: Hoffmann-La Roche Inc., Nutley, N.J.

[21] Appl. No.: 186,051

[22] Filed: Sep. 11, 1980

Related U.S. Application Data

[62] Division of Ser. No. 63,288, Aug. 2, 1979.

[30] Foreign Application Priority Data

Aug. 11, 1978 [CH] Switzerland .................. 8563/78
Jun. 6, 1979 [CH] Switzerland .................. 5270/79
Jul. 5, 1979 [CH] Switzerland .................. 6296/79

[51] Int. Cl.³ .............................................. C07C 127/19
[52] U.S. Cl. .................................. 564/51; 260/239 E; 260/326.4; 260/326.43; 544/59; 544/164; 544/390; 548/200; 560/251; 564/50
[58] Field of Search .................................. 564/50, 51; 260/239.3 D, 239 E, 326.4, 326.43; 544/59, 164, 390; 548/200; 560/251

[56] References Cited

U.S. PATENT DOCUMENTS 3,329,701  7/1967  Saucy et al. ............ 260/239.3 D X
3,910,911  10/1975 Ishizumi et al. .............. 564/50 X
4,141,895  2/1979  Middleton ................... 564/50 X Primary Examiner—Thomas A. Waltz
Attorney, Agent, or Firm—Jon S. Saxe; Bernard S. Leon; Frank P. Hoffman

[57] ABSTRACT

This invention provides benzodiazepine derivatives of the general formula

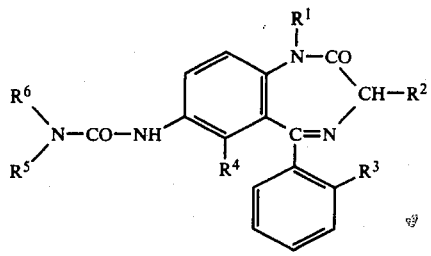

wherein $R^1$ represents a lower alkyl group, $R^2$ represents a hydrogen atom or a lower alkyl group, $R^3$ represents a halogen atom and $R^4$ represents a hydrogen or halogen atom and either $R^5$ represents a hydrogen atom or a lower alkyl group and $R^6$ represents a lower alkyl, lower hydroxyalkyl or lower acyloxyalkyl group or $R^5$ represents a hydrogen atom and $R^6$ represents an aryl or lower aralkyl group or $R^5$ and $R^6$ together with the nitrogen atom to which they are attached represent a 3-membered to 7-membered heterocycle which, when it is at least 5-membered, can contain as a ring member an oxygen or sulphur atom or a group of the formula $>N-R^7$ in which $R^7$ represents a hydrogen atom or a lower alkyl group, and pharmaceutically acceptable acid addition salts thereof, which possess aldosterone-antagonistic properties and are accordingly suitable for the control or prevention of heart failure, of hepatic ascites, of primary aldosteronism and of idiopathic hypertension. Some of these compounds and salts also inhibit the intestinal resorption of cholesterol and are according suitable for the prevention or control of atherosclerosis. Also provided are a process for the manufacture of the above end products and novel intermediates therefor.

2 Claims, No Drawings

N'[3-(HALOBENZOYL)-4-(GLYCYLAMINO)-PHENYL]UREAS

This is a division of application Ser. No. 63,288, filed Aug. 2, 1979.

DESCRIPTION OF THE INVENTION

The present invention relates to benzodiazepine derivatives. More particularly, the invention is concerned with benzodiazepine derivatives of the general formula

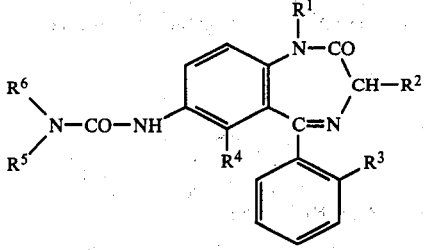

wherein $R^1$ represents a lower alkyl group, $R^2$ represents a hydrogen atom or a lower alkyl group, $R^3$ represents a halogen atom and $R^4$ represents a hydrogen or halogen atom and either $R^5$ represents a hydrogen atom or a lower alkyl group and $R^6$ represents a lower alkyl, lower hydroxyalkyl or lower acyloxyalkyl group or $R^5$ represents a hydrogen atom and $R^6$ represents an aryl or lower aralkyl group or $R^5$ and $R^6$ together with the nitrogen atom to which they are attached represent a 3-membered to 7-membered heterocycle which, when it is at least 5-membered, can contain as a ring member an oxygen or sulphur atom or a group of the formula $>$N—$R^7$ in which $R^7$ represents a hydrogen atom or a lower alkyl group, and pharmaceutically acceptable acid addition salts thereof.

Objects of the present invention are benzodiazepine derivatives of the foregoing formula I and pharmaceutically acceptable acid addition salts thereof, the manufacture of said derivatives and salts, intermediates for the manufacture of said derivatives, medicaments containing one or more benzodiazepine derivatives of formula I or pharmaceutically acceptable acid addition salts thereof, the manufacture of such preparations as well as the use of benzodiazepine derivatives of formula I and of pharmaceutically acceptable acid addition salts thereof in the control or prevention of illnesses.

As used in this Specification, the term "lower alkyl", alone or in combinations such as in "lower hydroxyalkyl" and the like denotes straight-chain or branched-chain saturated hydrocarbon groups containing at most 7, preferably at most 4, carbon atoms such as methyl, ethyl, n-propyl, isopropyl, n-butyl, tert.butyl etc. The term "lower hydroxyalkyl" includes groups such as 2-hydroxyethyl, 3-hydroxy-2-propyl and the like. The lower acyloxyalkyl groups are lower alkyl groups substituted by lower acyloxy groups and there primarily come into consideration lower alkyl groups substituted by lower alkanoyloxy groups, for example lower acetoxyalkyl groups such as 2-acetoxyethyl. As aryl groups there primarily come into consideration the phenyl group or substituted phenyl groups, for example a phenyl group monosubstituted by halogen or lower alkoxy such as p-chlorophenyl or p-methoxyphenyl.

The term "lower aralkyl" means a lower alkyl group substituted by an aryl group such as, for example, benzyl. When $R^5$ and $R^6$ together with the nitrogen atom to which they are attached represent a 3-membered to 7-membered heterocycle, then there primarily come into consideration aziridine, pyrrolidine, N-methylpiperazine, thiazolidine, morpholine and thiomorpholine groups.

Preferred among the compounds of formula I are those in which $R^2$ represents a hydrogen atom. In formula I, $R^3$ preferably represents a fluorine atom and $R^4$ preferably represents a hydrogen or chlorine atom.

A quite especially preferred compound of formula I is 1-[5-(o-fluorophenyl)-2,3-dihydro-1-methyl-2-oxo-1H-1,4-benzodiazepin-7-yl]-3-(2-hydroxyethyl)urea. Other compounds of formula I which are especially preferred are 1-[5-(o-fluorophenyl)-2,3-dihydro-1-methyl-2-oxo-1H-1,4-benzodiazepin-7-yl]-3-methylurea, 1-[5-(o-fluorophenyl)-2,3-dihydro-1-methyl-2-oxo-1H-1,4-benzodiazepin-7-yl]-3-(2-hydroxy-1-methylethyl)urea, N-[5-(o-fluorophenyl)-2,3-dihydro-1-methyl-2-oxo-1H-1,4-benzodiazepin-7-yl]-1-pyrrolidinecarboxamide, 1-[6-chloro-5-(o-fluorophenyl)-2,3-dihydro-1-methyl-2-oxo-1H-1,4-benzodiazepin-7-yl]-3-methylurea, 1-n-butyl-3-[6-chloro-5-(o-fluorophenyl)-2,3-dihydro-1-methyl-2-oxo-1H-1,4-benzodiazepin-7-yl]urea and 3-[6-chloro-5-(o-fluorophenyl)-2,3-dihydro-1-methyl-2-oxo-1H-1,4-benzodiazepin-7-yl]-1-ethyl-1-methylurea, as well as 1-tert.butyl-3-[5-(o-fluorophenyl)-2,3-dihydro-1-methyl-2-oxo-1H-1,4-benzodiazepin-7-yl]urea, 1-[5-(o-fluorophenyl)-2,3-dihydro-1-methyl-2-oxo-1H-1,4-benzodiazepin-7-yl]-3-(p-methoxyphenyl)urea, 1-benzyl-3-[5-(o-fluorophenyl)-2,3-dihydro-1-methyl-2-oxo-1H-1,4-benzodiazepin-7-yl]urea, 3-[5-(o-fluorophenyl)-2,3-dihydro-1-methyl-2-oxo-1H-1,4-benzodiazepin-7-yl]-1,1-dimethylurea, 1-ethyl-3-[5-(o-fluorophenyl)-2,3-dihydro-1-methyl-2-oxo-1H-1,4-benzodiazepin-7-yl]-1-methylurea, N-[5-(o-fluorophenyl)-2,3-dihydro-1-methyl-2-oxo-1H-1,4-benzodiazepin-7-yl]-1-aziridinecarboxamide, 1-[6-chloro-5-(o-fluorophenyl)-2,3-dihydro-1-methyl-2-oxo-1H-1,4-benzodiazepin-7-yl]-3-ethylurea, 1-[6-chloro-5-(o-fluorophenyl)-2,3-dihydro-1-methyl-2-oxo-1H-1,4-benzodiazepin-7-yl]-3-(2-hydroxyethyl)urea and 3-[6-chloro-5-(o-fluorophenyl)-2,3-dihydro-1-methyl-2-oxo-1H-1,4-benzodiazepin-7-yl]-1,1-diethylurea.

According to the process provided by the present invention, the benzodiazepine derivatives aforesaid (i.e. the compounds of formula I and their pharmaceutically acceptable acid addition salts) are manufactured by (a) reacting a benzodiazepine derivative of the general formula

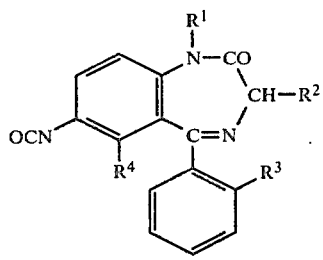

wherein $R^1$, $R^2$, $R^3$ and $R^4$ have the significance given earlier, with an amino compound of the general formula

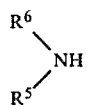

wherein $R^5$ and $R^6$ have the significance given earlier, or (b) cyclising a compound of the general formula

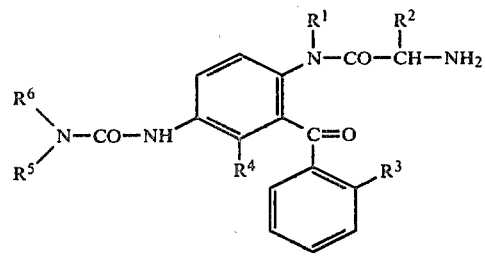

wherein $R^1$, $R^2$, $R^3$, $R^4$, $R^5$ and $R^6$ have the significance given earlier, or (c) reacting a benzodiazepine derivative of the general formula

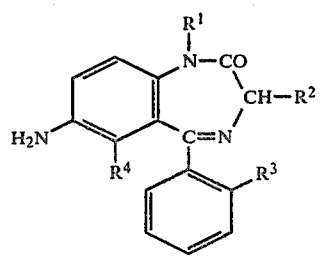

wherein $R^1$, $R^2$, $R^3$ and $R^4$ have the significance given earlier, with a halide of the general formula

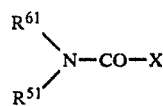

wherein X represents a halogen atom and either $R^{51}$ represents a lower alkyl group and $R^{61}$ represents a lower alkyl or a lower acyloxyalkyl group or $R^{51}$ and $R^{61}$ together with the nitrogen atom to which they are attached represent a 3-membered to 7-membered heterocycle which, when it is at least 5-membered, can contain as a ring member an oxygen or sulphur atom or a group of the formula $>N-R^{71}$ in which $R^{71}$ represents a lower alkyl group, or (d) reacting a benzodiazepine derivative of formula V hereinbefore with an isocyanate of the general formula $$R^{62}-NCO \qquad VII$$

wherein $R^{62}$ represents a lower alkyl, lower acyloxyalkyl, aryl or lower aralkyl group, or (e) removing the protecting group(s) from a benzodiazepine derivative of the general formula

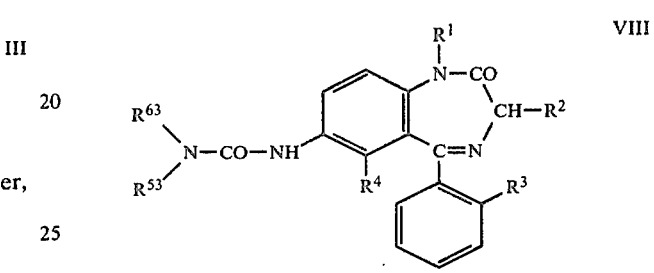

wherein $R^1$, $R^2$, $R^3$ and $R^4$ have the significance given earlier and either $R^{53}$ represents a protecting group and $R^{63}$ represents a lower alkyl, aryl or lower aralkyl group or a group of the formula $$-A-O-Y \qquad IX$$

in which A represents a lower alkylene group and Y represents a protecting group, or $R^{53}$ represents a hydrogen atom or a lower alkyl group and $R^{63}$ represents a group of formula IX hereinbefore or $R^{53}$ and $R^{63}$ together with the nitrogen atom to which they are attached represent a 5-membered to 7-membered heterocycle which contains as a ring member a group of the formula $>N-Z$ in which Z represents a protecting group, or (f) converting a benzodiazepine derivative of the general formula

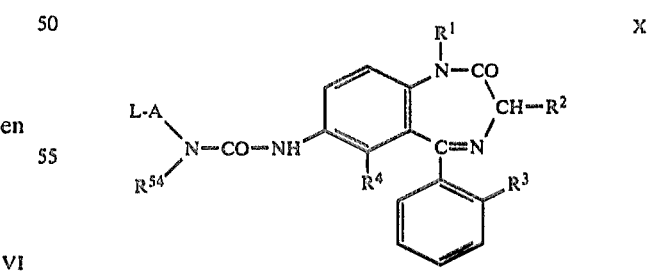

wherein $R^1$, $R^2$, $R^3$, $R^4$ and A have the significance given earlier, $R^{54}$ represents a hydrogen atom or a lower alkyl group and L represents a leaving group, into a corresponding hydroxy or acyloxy compound, or (g) acylating a benzodiazepine derivative of the general formula

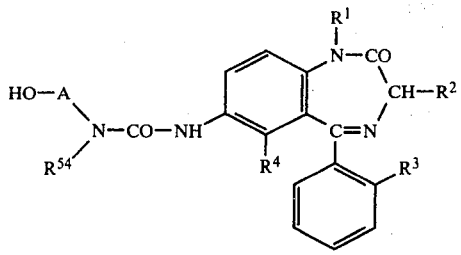

wherein $R^1$, $R^2$, $R^3$, $R^4$, $R^{54}$ and A have the significance given earlier, or (h) hydrolytically opening the aziridine ring in a benzodiazepine derivative of the general formula

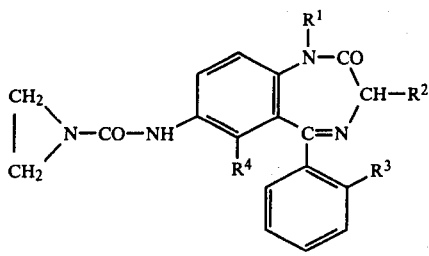

wherein $R^1$, $R^2$, $R^3$ and $R^4$ have the significance given earlier, or (i) converting a benzodiazepine derivative of formula I into a pharmaceutically acceptable acid addition salt.

According to embodiment (a) of the process, the benzodiazepine derivatives of formula I are manufactured from benzodiazepine derivatives of formula II and amino compounds of formula III. In this case, the benzodiazepine derivative of formula II is conveniently prepared in the manner described hereinafter from the corresponding benzodiazepine derivative of formula V shortly or immediately before the reaction with the amino compound of formula III and is introduced into the reaction not in isolated form but in the solution in which it has previously been prepared from the corresponding benzodiazepine derivative of formula V.

An amino compound of formula III can then be added to the aforementioned solution containing the benzodiazepine derivative of formula II. In so doing, the amino compound of formula III can be used in the form of a solution or in the absence of a solvent. Where an amino compound which is gaseous at room temperature is used (e.g. in the case of methylamine), it can be introduced as the gas into the aforementioned solution containing the benzodiazepine derivative of formula II.

On the other hand, it is also possible to provide the amino compound of formula III, conveniently in the form of a solution, and then to add thereto the aforementioned solution containing the benzodiazepine derivative of formula II.

In many cases it is convenient to use an excess of the amino compound of formula III and this is indeed necessary when it contains more than 1 nitrogen atom which is capable of reacting with an isocyanate group (e.g. in the case of piperazine).

Various organic solvents which are inert under the reaction conditions (e.g. halogenated hydrocarbons such as dichloroethane, methylene chloride, chloroform, o-dichlorobenzene etc, ethers such as tetrahydrofuran, dioxan, dimethoxyethane, diethyleneglycol dimethyl ether etc or the like) are suitable as the solvent for embodiment (a) of the process.

The reaction of a compound of formula II with an amino compound of formula III is conveniently carried out at room temperature or at a temperature below room temperature. When a solution of the benzodiazepine derivative of formula II is provided, the amino compound of formula III should be added within a short time, whereas in the opposite case (i.e. when the amino compound of formula III is provided and the solution of the benzodiazepine derivative of formula II is added thereto) the promptness with which the addition is carried out is not critical.

According to embodiment (b) of the process, the benzodiazepine derivatives of formula I are manufactured by cyclising a compound of formula IV. The cyclisation of a compound of formula IV is carried out relatively readily; it can be expedited, if necessary, by standing for a long time and/or by the use of heat. The cyclisation can be carried out in a neutral, alkaline or acidic medium, preferably in an alkaline medium. The cyclisation is conveniently carried out in an inert organic solvent; for example, a hydrocarbon such as benzene, toluene etc, a chlorinated hydrocarbon such as chloroform, methylene chloride etc, an ether such as dioxan etc. Suitable temperatures for the cyclisation of the compounds of formula IV are temperatures between room temperature and about 150° C. depending, of course, on the solvent used.

The compounds of formula IV need not necessarily be used in isolated form and in many cases this is not possible. Generally, it has been found to be convenient to cyclise the compounds of formula IV directly or to leave them to cyclise without isolation from the mixture in which they have been prepared.

According to embodiment (c) of the process, benzodiazepine derivatives of formula I are manufactured by reacting a benzodiazepine derivative of formula V with a halide of formula VI. This reaction is carried out in the presence of an acid-binding agent; for example, an inorganic base such as potassium carbonate, sodium carbonate etc or an organic base such as a tertiary amino compound (e.g. triethylamine, N-ethyl-diisopropylamine, quinuclidine etc).

The reaction of a benzodiazepine derivative of formula V with a halide of formula VI is conveniently carried out at room temperature or at a temperature below room temperature. The reaction proceeds relatively slowly and generally takes several days.

According to embodiment (d) of the process, benzodiazepine derivatives of formula I are manufactured by reacting a benzodiazepine derivative of formula V with an isocyanate of formula VII. This reaction is conveniently carried out in an organic solvent which is inert under the reaction conditions; for example, a halogenated hydrocarbon such as methylene chloride, dichloroethane, chloroform, o-dichlorobenzene etc, an ether such as tetrahydrofuran, dioxan, dimethoxyethane, diethyleneglycol dimethyl ether etc or the like. In many cases it has been found to be favourable to carry out the reaction in the presence of a catalytically-acting small amount of a base; for example, a tertiary amino compound such as triethylamine, N-ethyl-diisopropylamine, quinuclidine etc. The temperature at which this reaction is carried out is not critical and the reaction can be carried out at room temperature, at a temperature below room temperature or at a temperature above room temperature (e.g. at the reflux temperature).

According to embodiment (e) of the process, benzodiazepine derivatives of formula I can be manufactured by removing the protecting group or the protecting groups from a benzodiazepine derivative of formula VIII. Suitable nitrogen-protecting groups for the purpose of the present invention are primarily acyl groups, preferably readily cleavable alkoxycarbonyl or aralkoxycarbonyl groups, especially tert.butoxycarbonyl, benzyloxycarbonyl etc as well as readily cleavable aralkyl groups such as benzyl. Suitable oxygen-protecting groups are on the one hand acyl groups or aralkyl groups such as those mentioned earlier as nitrogen-protecting groups and on the other hand ketal protecting groups such as tetrahydropyranyl, 2-methoxy-2-propyl, methoxymethyl, β-methoxy-ethoxy-methyl etc or readily cleavable alkyl groups such as tert.butyl or alkanoyl groups such as acetyl etc.

The removal of the protecting groups or of the protecting groups from the benzodiazepine derivatives of formula VIII is carried out according to methods known per se, whereby, of course, the nature of the protecting group or protecting groups to be removed must be taken into consideration when choosing the method or methods used for the removal. In addition, it will, of course, be appreciated that only those methods can be used which selectively remove the protecting group or protecting groups without affecting other structural elements present in the molecule.

The groups mentioned earlier as examples of protecting groups can be cleaved off, depending on their nature, hydrogenolytically and/or hydrolytically. Thus, for example, the benzyloxycarbonyl group and the tert.butoxycarbonyl group can be cleaved off under selective acidic conditions; for example, by treatment with a mixture of hydrogen bromide and glacial acetic acid or by treatment with boron trifluoride or boron tribromide in an inert organic solvent such as dichloromethane. The tert.butoxycarbonyl group can also be cleaved off by treatment with hydrogen chloride in an inert organic solvent such as dioxan, tetrahydrofuran or the like or by treatment with trifluoroacetic acid. The tetrahydropyranyl group can be cleaved off under mild acidic aqueous conditions; for example, by treatment with a dilute aqueous mineral acid under mild conditions. The tert.butyl group can be cleaved off, for example, using trifluoroacetic acid. The benzyl group can be cleaved off by catalytic hydrogenation (e.g. over palladium/carbon). The acetyl group can be cleaved off under mild alkaline conditions; for example, with a solution of a sodium alcoholate in a corresponding alcohol (e.g. methanolic sodium methylate).

According to embodiment (f) of the process, benzodiazepine derivatives of formula I can be manufactured by converting a benzodiazepine derivative of formula X into a corresponding hydroxy or acyloxy compound. The leaving group denoted by L in formula X can be a halogen atom, especially a chlorine, bromine or iodine atom or can be an equivalent leaving group (e.g. an arylsulphonyloxy group such as tosyloxy, an alkylsulphonyloxy group such as mesyloxy, a quaternary ammonium group such as the trimethylammonium group etc).

The conversion of a benzodiazepine derivative of formula X into a corresponding hydroxy compound can be carried out, for example by solvolysis in a water-containing system, conveniently in a mixture of an aromatic hydrocarbon (e.g. benzene) and water in the presence of a quaternary ammonium salt (e.g. tetrabutylammonium bromide) and at a temperature between room temperature and the reflux temperature of the mixture.

The conversion of a benzodiazepine derivative of formula X into a corresponding acyloxy compound is carried out by reaction with an alkali metal or alkaline earth metal salt of the organic acid corresponding to the acyloxy group to be introduced; for example, with an alkali metal salt of a lower alkanecarboxylic acid such as potassium acetate. The reaction is carried out in an organic solvent or solvent mixture which is inert under the reaction conditions; for example, in dimethylformamide, dimethyl sulphoxide, hexamethylphosphoric acid triamide etc. In the manufacture of an acetoxy compound, glacial acetic acid can also be used as the solvent. A solution of 18-crown-6 in acetonitrile is especially convenient. The reaction is conveniently carried out at a temperature between room temperature and the reflux temperature of the reaction mixture.

According to embodiment (g) of the process, benzodiazepine derivatives of formula I can be manufactured by acylating a benzodiazepine derivative of formula Ia. This acylation can be carried out with any suitable acylating agent; for example, an acid anhydride such as acetic acid anhydride, an acid halide such as acetyl chloride etc. The conditions under which the acylation is carried out can be readily selected by any person skilled in the art depending on the acylating agent which is used. For example, the acylation can be carried out at room temperature or at a temperature above or below room temperature. The acylation is conveniently carried out in an organic solvent which is inert under the acylation conditions (e.g. acetonitrile or the like, methylene chloride, dichloroethane or the like, tetrahydrofuran, dimethoxyethane or the like etc) and in the presence of an acid-binding agent (e.g. an inorganic base such as potassium carbonate, sodium carbonate etc or a teritary organic amino compound such as triethylamine, N-ethyl-diisopropylamine, quinuclidine etc).

According to embodiment (h) of the process, benzodiazepine derivatives of formula I are manufactured by hydrolytically opening the aziridine ring in a benzodiazepine derivative of formula Ib. This hydrolytic ring-opening is carried out under acidic conditions, there coming into consideration only those acids whose anion does not react with the aziridine ring. The hydrolytic ring-opening is conveniently carried out in the presence of a suitable organic solvent which is inert under the reaction conditions and at room temperature. For example, the hydrolytic ring-opening can be carried out by dissolving the benzodiazepine derivative of formula Ib in dioxan or the like, adding to the solution a small amount of a mineral acid (e.g. a few drops of 25% sulphuric acid) and leaving the mixture to stand but only for a short time (e.g. 15 to 30 minutes).

According to embodiment (i) of the process, the benzodiazepine derivatives of formula I can be converted into pharmaceutically acceptable acid addition salts. The manufacture of such pharmaceutically acceptable acid addition salts is carried out according to customary methods. There come into consideration not only salts with inorganic but also salts with organic acids; for example, hydrochlorides, hydrobromides, sulphates, citrates, acetates, succinates, methanesulphonates, p-toluenesulphonates and the like.

The benzodiazepine derivatives of formula II used as starting materials in embodiment (a) of the process can be prepared, as already mentioned earlier, from corresponding benzodiazepine derivatives of formula V. The compounds of formula V are converted into compounds of formula II by reaction with phosgene. Conveniently a solution of phosgene in an organic solvent which is inert under the reaction conditions is provided, a solution of benzodiazepine derivative of formula V is then added while cooling, the mixture is heated to reflux for a period and again cooled down, and finally the solution obtained is made basic or at least neutral with a tertiary organic amino compound such as triethylamine. The resulting solution, containing a benzodiazepine derivative of formula II, can be stored for several hours with the exclusion of moisture and in the cold; it is, as mentioned earlier, used directly in the process without isolation of the benzodiazepine derivative of formula II contained therein.

The benzodiazepine derivatives of formula II are novel and also form an object of the present invention. A representative benzodiazepine derivative of formula II is [5-(o-fluorophenyl)-2,3-dihydro-1-methyl-2-oxo-1H-1,4-benzodiazepin-7-yl]isocyanate.

Compounds of formula IV used as starting materials in embodiment (b) of the process can be prepared according to methods known per se; the preparative procedure being carried out, in part, in analogy to methods which are described earlier in connection with certain processes for the manufacture of benzodiazepine derivatives of formula I and described hereinafter in connection with the preparation of benzodiazepine derivatives of formula VIII. As starting materials for the preparation of the compounds of formula IV there are conveniently used benzophenone derivatives of the general formula

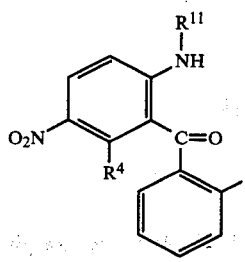

XI wherein $R^3$ and $R^4$ have the significance given earlier and $R^{11}$ represents a hydrogen atom or a lower alkyl group.

For example, a benzophenone derivative of formula XI can initially be converted into a compound of the general formula

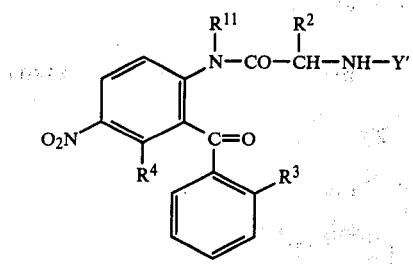

XII wherein $R^2$, $R^3$, $R^4$ and $R^{11}$ have the significance given earlier and Y' represents a protecting group, whereupon, where $R^{11}$ in formulae XI and XII represents a hydrogen atom, the nitrogen atom is alkylated, the nitro group is reduced to the amino group and, where $R^4$ in formulae XI and XII represents a hydrogen atom, the resulting amino compound is halogenated if desired. Suitable protecting groups denoted by Y' in formula XII are primarily acyl groups, preferably readily cleavable alkoxycarbonyl or aralkoxycarbonyl groups, especially the benzyloxycarbonyl group. Accordingly, for the preparation of the compounds of formula XII from the benzophenone derivatives of formula XI there are conveniently used corresponding acylaminoalkanoyl halides such as carbobenzoxyglycine chloride, carbobenzoxyalanine chloride, carbobenzoxy-α-aminobutyric acid chloride etc. Where it is necessary to carry out a N-alkylation, then this is carried out according to methods known per se; for example, using methyl iodide or the like in the presence of a base such as potassium carbonate and in a suitable solvent which is inert under the reaction conditions such as acetone. The reduction of the nitro to the amino group is conveniently effected with stannous chloride and the like. An optional halogenation of 5-aminobenzophenone derivatives which are unsubstituted in the 6-position is conveniently carried out using elemental halogen in an acidic aqueous solution, there being preferably used as the acid the hydrogen halide corresponding to the halogen atom to be introduced.

The 5-aminobenzophenone derivatives of the general formula

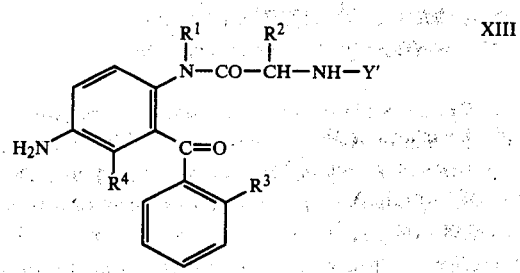

XIII wherein $R^1$, $R^2$, $R^3$, $R^4$ and Y' have the significance given earlier, obtained in the manner previously described are subsequently converted into corresponding compounds of the general formula

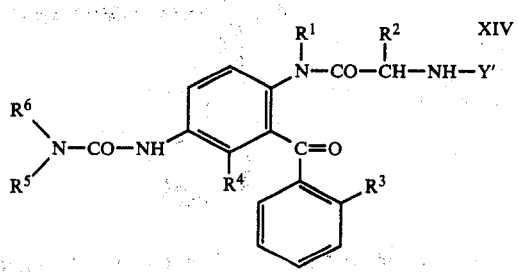

XIV wherein $R^1$, $R^2$, $R^3$, $R^4$, $R_5$, $R^6$ and Y' have the significance given earlier.

This can be carried out, for example, by reacting a 5-aminobenzophenone derivative of formula XIII in analogy to methods described earlier with a halide of formula VI or an isocyanate of formula VII or by converting a 5-aminobenzophenone derivative of formula XIII, in analogy to the method described earlier for the manufacture of the benzophenodiazepine derivatives of formula II, into a corresponding isocyanate which is then reacted with an amino compound of formula III in analogy to the method described earlier for the manufacture of benzodiazepine derivatives of formula I from benzodiazepine derivatives of formula II and amino compounds of formula III.

A corresponding compound of formula IV is then obtained by cleaving off the protecting group denoted by Y' from a compound of formula XIV.

It is also possible to convert (in analogy to the method described hereinafter for the preparation of the benzodiazepine derivatives of formula X) a compound of formula XIII into a compound of the general formula

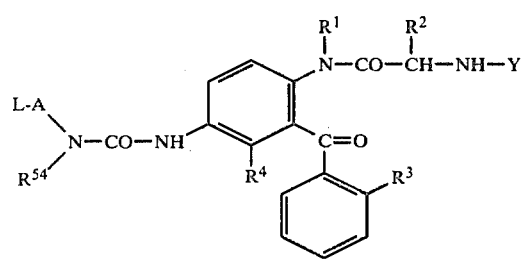

wherein $R^1$, $R^2$, $R^3$, $R^4$, $R^{54}$, L, A and Y' have the significance given earlier, thereupon to convert (in analogy to the method described earlier for the manufacture of benzodiazepine derivatives of formula I from benzodiazepine derivatives of formula X) a compound of formula XV into a corresponding hydroxy or acyloxy compound and thereupon to proceed to the corresponding compound of formula IV by cleaving off the protecting group denoted by Y'. Furthermore, it is possible to convert a compound of formula XIII into a compound of the general formula

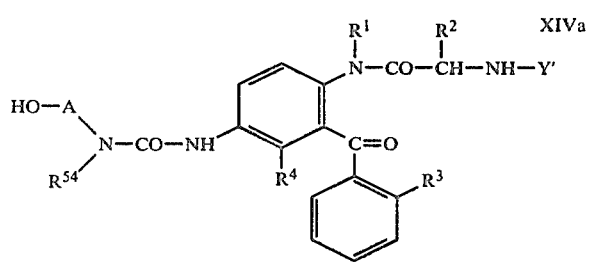

wherein $R^1$, $R^2$, $R^3$, $R^4$, $R^{54}$, A and Y' have the significance given earlier, whereupon a corresponding compound of formula IV can be obtained by acylation (in analogy to the method described earlier for the manufacture of benzodiazepine derivatives of formula I from benzodiazepine derivatives of formula Ia) and subsequent cleavage of the protecting group denoted by Y'.

Furthermore, it is possible to convert a compound of formula XIII into a compound of the general formula

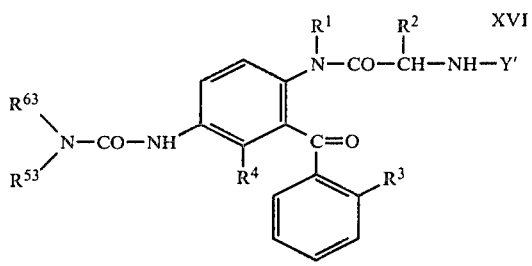

wherein $R^1$, $R^2$, $R^3$, $R^4$, $R^{53}$, $R_{63}$ and Y' have the significance given earlier.

This conversion can be carried out in analogy to the methods described hereinafter for the manufacture of the benzodiazepine derivatives of formula VIII. Compounds of formula IV are then prepared from compounds of formula XVI by cleaving off the protecting group denoted by Y' and, previously or in the same operation, the other protecting group or other protecting groups present in the molecule.

A further possibility for the preparation of the compounds of formula IV consists in converting a nitrobenzophenone derivative of formula XI into a compound of the general formula

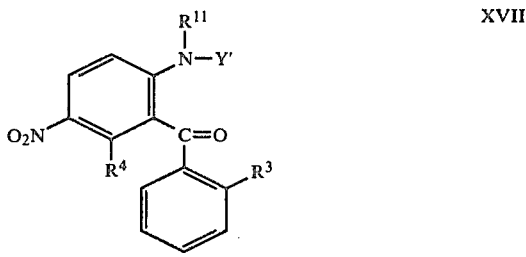

wherein $R^3$, $R^4$, $R^{11}$ and Y' have the significance given earlier, thereupon, where $R^{11}$ in formula XVII represents a hydrogen atom, alkylating the nitrogen atom, reducing the nitro group and, if desired, halogenating a 5-aminobenzophenone derivative which is unsubstituted in the 6-position. The compounds obtained in this manner have the general formula

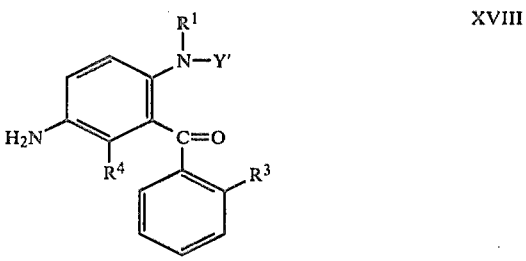

wherein $R^1$, $R^3$, $R^4$ and Y' have the significance given earlier.

A compound of formula XVIII can then be converted into a compound of the formula

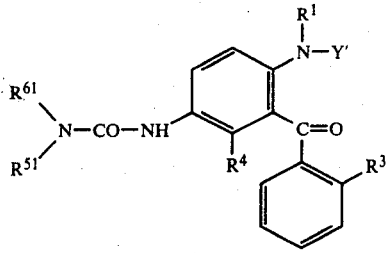

or

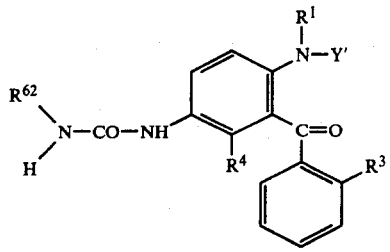

wherein $R^1$, $R^3$, $R^4$, $R^{51}$, $R^{61}$, $R^{62}$ and $Y'$ have the significance given earlier, for example, by reaction with a halide of formula VI or an isocyanate of formula VII (in analogy to the method described earlier for the manufacture of benzodiazepine derivatives of formula I from benzodiazepine derivatives of formula V) or by conversion into a corresponding isocyanate (in analogy to the method described earlier for the preparation of benzodiazepine derivatives of formula II) and subsequent reaction of said isocyanate with an amino compound of the general formula

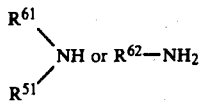

XX      XX' wherein $R^{51}$, $R^{61}$ and $R^{62}$ have the significance given earlier, (in analogy to the method described earlier for the manufacture of benzodiazepine derivatives of formula I from benzodiazepine derivatives of formula II). By cleaving off the protecting group denoted by $Y'$ from a compound of formula XIX or XIX' there is obtained a benzophenone derivative of the general formula

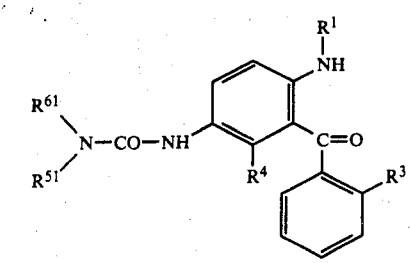

or

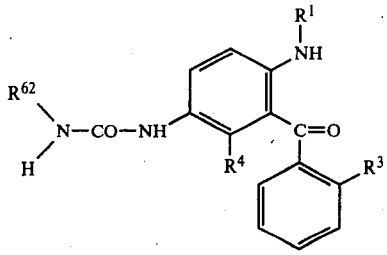

wherein $R^1$, $R^3$, $R^4$, $R^{51}$, $R^{61}$ and $R^{62}$ have the significance given earlier.

Benzophenone derivatives of formula XXI or XXI' can be converted according to a large number of different methods known per se into corresponding compounds of formula IV; for example, by reaction with a corresponding α-haloalkanoyl halide and treatment of the resulting compound with ammonia, by treatment with a corresponding α-aminoacylating agent carrying a suitable protecting group on the nitrogen atom (e.g. a corresponding α-benzyloxycarbonylaminoalkanoyl halide such as carbobenzoxyglycine chloride) and subsequent cleavage of the protecting group, by conversion into a corresponding α-azidoalkanoyl derivative (e.g. an azidoacetyl derivative) and subsequent reduction etc.

On the other hand, compounds of formula XVIII can also be converted (for example in analogy to the methods described hereinafter for the preparation of benzodiazepine derivatives of formula VIII) into corresponding compounds of the general formula

XXII wherein $R^1$, $R^3$, $R^4$, $R^{53}$, $R^{63}$ and $Y'$ have the significance given earlier, whereupon the protecting group denoted by $Y'$ is removed. It will be appreciated that the various protecting groups in a compound of formula XXII must be provided so that the protecting group denoted by $Y'$ can be removed without bringing about a cleavage of the other protecting group or protecting groups present in the molecule. A resulting compound is then converted according to methods known per se into a corresponding compound of formula XVI. This conversion can be carried out in analogy to the method described earlier for the preparation of the compounds of formula XII from the benzophenone derivatives of formula XI. The conversion of the compounds of formula XVI into corresponding compounds of formula IV has already been described earlier.

As already mentioned earlier, it is not necessary (and in many cases also not possible) to isolate the compounds of formula IV. On the contrary, it has generally been found to be convenient to cyclise these compounds directly or to leave these compounds to cyclise without isolation from the mixture in which they have been prepared.

The compounds of formula IV are novel and also form an object of the present invention. A representative compound of formula IV is N-hydroxyethyl-N'-[3-(o-fluorobenzoyl) (4-glycylamino)phenyl]urea.

The benzodiazepine derivatives of formula V used as starting materials in embodiment (c) of the process belong to a class of compound known per se and many specific representatives of this class of compound have already been described in the literature. Representatives which have not previously been specifically described can be prepared according to methods which are familiar to any person skilled in the art. Conveniently, benzodiazepine derivatives of formula V are prepared from corresponding nitro compounds of the general formula

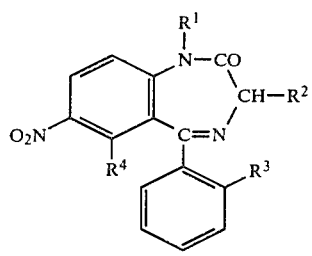

XXIII wherein $R^1$, $R^2$, $R^3$ and $R^4$ have the significance given earlier.

These nitro compounds likewise belong to a class of compound known per se of which various specific representatives are described in the literature. Representatives which have not previously been specifically described can be prepared according to methods which are familiar to any person skilled in the art and which can be carried out in analogy to those methods which are described for the preparation of the specifically previously known compounds. Moreover, various of the following Examples contain detailed information concerning the preparation of certain nitro compounds of formula XXIII.

The conversion of a nitro compound of formula XXIII into a corresponding benzodiazepine derivative of formula V is carried out by reduction of the nitro group, conveniently using stannous chloride, zinc, catalytically activated hydrogen etc. Where $R^4$ in formula XXIII represents a hydrogen atom and a benzodiazepine derivative of formula V in which $R^4$ represents a halogen atom is desired, a halogenation must be carried out subsequent to the aforementioned reduction. This halogenation is conveniently carried out using elemental halogen in acidic aqueous solution, there being conveniently used as the acid the hydrogen halide corresponding to the halogen atom to be introduced.

Benzodiazepine derivatives of formula VIII used as starting materials in embodiment (e) of the process can be prepared from benzodiazepine derivatives of formulae II or V according to various methods known per se. It will, of course, be appreciated that the nature of the protecting group or protecting groups whose presence is desired in one benzodiazepine derivative of formula VIII to be prepared must be taken into consideration when choosing the method or methods used.

For the preparation of a benzodiazepine derivative of formula VIII in which $R^{53}$ represents a protecting group, a benzodiazepine derivative of formula V can be reacted with a corresponding carbamoyl halide (in analogy to the method described earlier for the manufacture of benzodiazepine derivatives of formula I from benzodiazepine derivatives of formula V and halides of formula VI).

For the preparation of benzodiazepine derivatives of formula VIII in which $R^{53}$ represents a hydrogen atom and $R^{63}$ represents a group of formula IX, a benzodiazepine derivative of formula V can be reacted with a corresponding isocyanate (in analogy to the method described earlier for the manufacture of benzodiazepine derivatives of formula I from benzodiazepine derivatives of formula V and isocyanates of formula VII). A further possibility consists of reacting a benzodiazepine derivative of formula II with a corresponding amine (in analogy to the method described earlier for the manufacture of benzodiazepine derivatives of formula I from benzodiazepine derivatives of formula II and amino compounds of formula III). In this case, however, it should be noted that the protecting group denoted by Y can not be an acyl group. Furthermore, the aziridine ring in a benzodiazepine derivative of formula Ib can be opened by acid alcoholysis with tert.butanol, benzyl alcohol or the like to give a benzodiazepine derivative of formula VIII in which $R^{53}$ represents a hydrogen atom and $R^{63}$ represents the 2-tert.butoxyethyl, 2-benzyloxyethyl or like group.

For the preparation of benzodiazepine derivatives of formula VIII in which $R^{53}$ represents a lower alkyl group and $R^{63}$ represents a group of formula IX, a benzodiazepine derivative of formula V can be reacted with a corresponding carbamoyl halide (in analogy to the method described earlier for the manufacture of benzodiazepine derivatives of formula I from benzodiazepine derivatives of formula V and isocyanates of formula VI). Another possibility consists in reacting a benzodiazepine derivative of formula II with a corresponding amine (in analogy to the method described earlier for the manufacture of benzodiazepine derivatives of formula I from benzodiazepine derivatives of formula II and amino compounds of formula III). Again, in this case, the protecting group denoted by Y can not be an acyl group.

For the preparation of benzodiazepine derivatives of formula VIII in which $R^{53}$ and $R^{63}$ together with the nitrogen atom to which they are attached represent a 5-membered to 7-membered heterocycle which contains as a ring member a group of the formula

wherein Z represents a protecting group, either a benzodiazepine derivative of formula V can be reacted with a corresponding carbamoyl halide (in analogy to the method described earlier for the manufacture of benzodiazepine derivatives of formula I from benzodiazepine derivatives of formula V and halides of formula VI) or a benzodiazepine derivative of formula II can be reacted with a corresponding amine (in analogy to the method described earlier for the manufacture of benzodiazepine derivatives of formula I from benzodiazepine derivatives of formula II and amino compounds of formula III).

It will be appreciated that those benzodiazepine derivatives of formula VIII in which $R^{53}$ represents a hydrogen atom or a lower alkyl group and $R^{63}$ represents a group of formula IX in which the protecting group denoted by Y is a lower acyl group (e.g. acetyl) fall within formula I hereinbefore; namely, said benzodiazepine derivatives of formula VIII correspond to the benzodiazepine derivatives of formula I in which $R^5$ represents a hydrogen atom and $R^6$ represents a lower acyloxyalkyl group (e.g. lower acetoxyalkyl). The benzodiazepine derivatives of formula VIII which do not fall within formula I, namely those in which $R^{53}$ represents a protecting group when $R^{63}$ represents a group of formula IX and the protecting group denoted by Y is a lower acyl group, are novel and also form an object of the present invention. Among these novel benzodiazepine derivatives there are especially preferred those in which $R^1$ represents a methyl group, $R^2$ represents a hydrogen atom, $R^3$ represents a fluorine atom, $R^4$ represents a hydrogen atom, $R^{53}$ represents a hydrogen atom or a protecting group and $R^{63}$ represents a group of formula IX in which A represents a dimethylene group such as, for example, 1-(2-tert.butoxyethyl)-3-[5-(o-fluorophenyl)-2,3-dihydro-1-methyl-2-oxo-1H-1,4-benzodiazepin-7-yl]urea.

Benzodiazepine derivatives of formula X used as starting materials in embodiment (f) of the process can be prepared according to methods known per se from benzodiazepine derivatives of formula V by reaction with a corresponding carbamoyl chloride (in analogy to the method described earlier for the manufacture of benzodiazepine derivatives of formula I from benzodiazepine derivatives of formula V and halides of formula VI) or by reaction with a corresponding isocyanate (in analogy to the method described earlier for the manufacture of benzodiazepine derivatives of formula I from benzodiazepine derivatives of formula V and isocyanates of formula VII).

The benzodiazepine derivatives of formula X are novel and also form an object of the present invention. Preferred benzodiazepine derivatives of formula X are those in which $R^1$ represents a methyl group, $R^2$ represents a hydrogen atom, $R^3$ represents a fluorine atom, $R^4$ represents a hydrogen atom, $R^{54}$ represents a hydrogen atom and A represents a dimethylene group, such as, for example, 1-(2-chloroethyl)-3-[5-(o-fluorophenyl)-2,3-dihydro-1-methyl-2-oxo-1H-1,4-benzodiazepin-7-yl]urea.

Surprisingly, it has been shown that the benzodiazepine derivatives of formula I hereinbefore display no or only very slight activity on the central nervous system, whereas they exhibit pronounced aldosterone-antagonistic properties. These aldosterone-antagonistic properties can be demonstrated in adrenalectomised rats as illustrated hereinafter.

If aldosterone is administered to adrenalectomised rats, then there is observed, in comparison with untreated animals, a pronounced reduction of the sodium excretion (sodium retention), an increased potassium excretion (potassium excretion) as well as a reduction of the excreted urine volume. If benzodiazepine derivatives of formula I are administered to the animals before the treatment with aldosterone, then there is observed, in comparison with the animals which are treated only with aldosterone (control animals), a pronounced increase of the sodium excretion (i.e. the sodium retention caused by aldosterone is antagonised), whereas the potassium excretion and the urine volume are influenced to a lesser extent.

The standard experiment is carried out as follows:

Female Holtzmann rats (150–180 g) are bilaterally adrenalectomised 70 to 74 hours before the beginning of the experiment. After the operation, the animals receive a customary rat dry feed and 0.9% sodium chloride solution for drinking. 16–17 hours before the beginning of the experiment the feed is removed from the animals, but they can still drink, as before, 0.9% sodium chloride solution ad libitum. At the beginning of the experiment the substance to be tested as an aldosterone-antagonist is administered to the animals by means of a stomach probe. 30 minutes later the animals receive a subcutaneous injection of 4 mmmg/kg of aldosterone. After a further 90 minutes, the urinary bladders of the animals are emptied by careful suprapubic pressure, whereupon the animals are placed individually in metabolic cages without food and without drink. The urine of the animals is then collected for 3 hours, whereupon their urinary bladders are once more emptied. The spontaneously excreted urine and the remaining urine obtained at the conclusion of the experiment by pressing-out the urinary bladders are collected in graduated centrifuge glasses. Sodium and potassium concentrations in the urine are determined with a flame photometer.

The following Table contains results obtained in the previously described experiment with representative benzodiazepine derivatives of formula I. In this Table there are given for each benzodiazepine derivative in question the dosage administered (in mg/kg p.o.) as well as the percentage variation in the urine volume, the sodium excretion and the potassium excretion in comparison with the control animals (i.e. in comparison with the animals treated only with aldosterone). Moreover, the Table contains data relating to the acute toxicity of the benzodiazepine derivatives investigated (LD 50 in mg/kg in the case of a single oral administration to mice).

TABLE

| $R^1$ | $R^2$ | $R^3$ | $R^4$ | $R^5$ | $R^6$ | Dosage mg/kg p.o. | Volume | $[Na^+]$ | $[K^+]$ | LD 50 mg/kg p.o. |
|---|---|---|---|---|---|---|---|---|---|---|
| | | | | | | | in %, based on control animals | | | |
| $CH_3$ | H | F | H | H | $CH_2CH_2OH$ | 0,1 | 85 | 247 | 121 | > 5000 |
| $CH_3$ | H | F | H | H | $CH_3$ | 3 | 95 | 182 | 84 | > 5000 |
| $CH_3$ | H | F | H | H | t.-$C_4H_9$ | 10 | 105 | 234 | 70 | 600–1200 |
| | | | | | | 1 | 194 | 236 | 132 | |
| $CH_3$ | H | F | H | H | $CH(CH_3)CH_2OH$ | 10 | 200 | 452 | 129 | > 5000 |
| | | | | | | 1 | 73 | 127 | 80 | |
| $CH_3$ | H | F | H | H | p-$CH_3O$—$C_6H_4$ | 10 | 117 | 240 | 145 | > 5000 |
| $CH_3$ | H | F | H | H | $CH_2C_6H_5$ | 1 | 139 | 255 | 153 | > 5000 |
| $CH_3$ | H | F | H | $CH_3$ | $CH_3$ | 10 | 102 | 190 | 91 | > 5000 |
| $CH_3$ | H | F | H | $CH_3$ | $C_2H_5$ | 1 | 100 | 291 | 97 | > 5000 |
| $CH_3$ | H | F | H | ($CH_2$)$_2$ | | 10 | 129 | 237 | 108 | > 5000 |
| | | | | | | 1 | 192 | 294 | 146 | |
| $CH_3$ | H | F | H | ($CH_2$)$_4$ | | 1 | 184 | 308 | 112 | > 5000 |
| $CH_3$ | H | F | Cl | H | $CH_3$ | 1 | 178 | 330 | 91 | 1250–2500 |
| $CH_3$ | H | F | Cl | H | $C_2H_5$ | 10 | 156 | 271 | 149 | 2500–5000 |

TABLE-continued

| $R^1$ | $R^2$ | $R^3$ | $R^4$ | $R^5$ | $R^6$ | Dosage mg/kg p.o. | Volume in %, based | $[Na^+]$ on control | $[K^+]$ animals | LD 50 mg/kg p.o. |
|---|---|---|---|---|---|---|---|---|---|---|
| $CH_3$ | H | F | Cl | H | $n\text{-}C_4H_9$ | 1 | 175 | 380 | 104 | > 5000 |
| $CH_3$ | H | F | Cl | H | $CH_2CH_2OH$ | 1 | 140 | 242 | 110 | > 5000 |
| $CH_3$ | H | F | Cl | $CH_3$ | $C_2H_5$ | 1 | 136 | 278 | 118 | 2500–5000 |
| $CH_3$ | H | F | Cl | $C_2H_5$ | $C_2H_5$ | 10 | 124 | 236 | 110 | > 5000 |

The benzodiazepine derivatives of formula I and their pharmaceutically acceptable acid addition salts can be used as medicaments, for example in the form of pharmaceutical preparations. The pharmaceutical preparations can be administered orally, for example in the form of tablets, coated tablets, dragées, hard and soft gelatin capsules, solutions, emulsions or suspensions. The administration can, however, also be carried out by the rectal route (e.g. in the form of suppositories) or by the parenteral route (e.g. in the form of injection solutions).

For the manufacture of tablets, coated tablets, dragées and hard gelatin capsules, the benzodiazepine derivatives of formula I and their pharmaceutically acceptable acid addition salts can be processed with pharmaceutical inert, inorganic or organic excipients. Examples of such excipients which can be used for tablets, dragées and hard gelatin capsules are lactose, maize starch or derivatives thereof, talc, stearic acid or salts thereof etc.

Suitable excipients for soft gelatin capsules are, for example, vegetable oils, waxes, fats, semi-solid and liquid polyols etc. Depending on the nature of the active ingredient, no excipients may, however, be necessary in the case of soft gelatin capsules.

Suitable excipients for the manufacture of solutions and syrups are, for example, water, polyols, saccharose, invert sugar, glucose and the like.

Suitable excipients for injection solutions are, for example, water, alcohols, polyols, glycerine, vegetable oils etc.

Suitable excipients for suppositories are, for example, natural or hardened oils, waxes, fats, semi-liquid or liquid polyols and the like.

The pharmaceutical preparations can, moreover, contain preserving agents, solubilising agents, stabilising agents, wetting agents, emulsifying agents, sweetening agents, colouring agents, flavouring agents, salts for the variation of the osmotic pressure, buffers, coating agents or antioxidants. They can also contain still other therapeutically valuable substances.

As mentioned earlier, medicaments containing one or more benzodiazepine derivatives of formula I or pharmaceutically acceptable acid addition salts thereof are also an object of the present invention as is a process for the manufacture of such medicaments, which process comprises bringing one or more benzodiazepine derivatives of formula I or pharmaceutically acceptable acid addition salts thereof into a galenical administration form. A further object of the present invention is, as mentioned earlier, the use of benzodiazepine derivatives of formula I and of pharmaceutically acceptable acid addition salts thereof in the control or prevention of illnesses, especially in the control or prevention of heart failure, of hepatic ascites, of primary aldosteronism and of idiopathic hypertension. The dosage can vary within wide limits and is, of course, adjusted to the individual requirements in each particular case. In general, in the case of oral administration a daily dosage of about 20 mg to about 1500 mg should be appropriate.

Some of the benzodiazepine derivatives of the general formula I hereinbefore are also inhibiting the intestinal resorption of cholesterol, and this is particularly true for those wherein $R^1$, $R^2$, $R^3$ and $R^4$ have the significance given earlier, $R^5$ represents a hydrogen atom and $R^6$ represents a lower alkyl group containing at least 2 carbon atoms or a lower hydroxyalkyl group as well as for those wherein $R^1$, $R^2$ and $R^3$ have the significance given earlier, $R^4$ represents a halogen atom and either $R^5$ and $R^6$ each represent a lower alkyl group or $R^5$ and $R^6$ together with the nitrogen atom to which they are attached represent a 3-membered to 7-membered heterocycle which, when it is at least 5-membered, can contain as a ring member an oxygen or sulphur atom or a group of the formula $>N-R^7$ in which $R^7$ has the significance given earlier. Preferred among these compounds are those wherein $R^3$ represents a fluorine or chlorine atom and wherein $R^4$ represents a halogen atom, with chlorine and particularly bromine being especially preferred.

A quite especially preferred compound of the present invention inhibiting the intestinal resorption of cholesterol is 1-[6-bromo-5-(o-chlorophenyl)-2,3-dihydro-1,3-dimethyl-2-oxo-1H-1,4-benzodiazepin-7-yl]-3-(2-hydroxyethyl)urea. This compound contains an asymmetric centre and can thus be present in racemic or optically active form. It will be appreciated that this is true for all compounds of formula I hereinbefore containing an asymmetric centre. Compounds of formula I hereinbefore containing more than one asymmetric centre can be present in various diastereoisomeric forms. The present invention encompasses all possible stereoisomers of compounds of formula I hereinbefore containing one or more asymmetric centres, all possible mixtures of diastereoisomers and all possible racemates as well as the separation of mixtures of diastereoisomers and the resolution of racemates which can be effected according to methods known per se.

Further particularly preferred compounds of the present invention inhibiting the intestinal resorption of cholesterol are N-[6-chloro-5-(o-fluorophenyl)-2,3-dihydro-1-methyl-2-oxo-1H-1,4-benzodiazepin-7-yl]-4-morpholinecarboxamide;

1-[6-bromo-5-(o-fluorophenyl)-2,3-dihydro-1,3-dimethyl-2-oxo-1H-1,4-benzodiazepin-7-yl]-3-(2-hydroxyethyl)urea; and 1-[6-chloro-5-(o-chlorophenyl)-2,3-dihydro-1,3-dimethyl-2-oxo-1H-1,4-benzodiazepin-7-yl]-3-(2-hydroxyethyl)urea.

The inhibition of the intestinal resorption of cholesterol can be demonstrated in the animal test described hereinafter:

The compounds to be tested are administered to groups of 6 normal female Füllinsdorf albino rats (body weight about 70 g) by oral intubation. This is followed immediately by oral intubation of a test meal containing radioactive cholesterol. Consecutively, feces are collected for three days, freeze dried and pulverized. An aliquot is burned for evaluation of fecal radioactivity. Controls excrete about 40–50% of the dietary radioactive cholesterol called cholesterol recovery (CHOREC) and arbitrarily set 100%. Animals treated with a substance inhibiting the intestinal resorption of cholesterol show a higher excretion of radioactive cholesterol in comparison with controls. The cholesterol recovery (CHOREC) of treated animals is expressed in % of controls.

The following Table contains results obtained with the aforementioned particularly preferred compounds inhibiting the intestinal resorption of cholesterol. For each of these compounds there are given the dose(s) administered (in μMol/kg p.o.) as well as the cholesterol recovery (CHOREC), expressed in % of controls. Moreover, the Table contains data relating to the acute toxicity of the compounds investigated (LD 50 in mg/kg in the case of a single oral administration to rats):

TABLE

| $R^1$ | $R^2$ | $R^3$ | $R^4$ | $R^5$ | $R^6$ | Dose μMol/kg p.o. | CHOREC % | LD 50 mg/kg p.o. |
|---|---|---|---|---|---|---|---|---|
| $CH_3$ | H | F | Cl | | $(CH_2)_2O(CH_2)_2$ | 1000 | 186 | 1250–2500 |
| $CH_3$ | $CH_3$ (rac.) | Cl | Cl | H | $CH_2CH_2OH$ | 1000 | 188 | > 5000 |
| $CH_3$ | $CH_3$ (rac.) | Cl | Br | H | $CH_2CH_2OH$ | 1000 | 187 | > 5000 |
| | | | | | | 100 | 168 | |
| | | | | | | 30 | 157 | |
| | | | | | | 10 | 150 | |
| $CH_3$ | $CH_3$ (rac.) | F | Br | H | $CH_2CH_2OH$ | 1000 | 189 | > 5000 |
| | | | | | | 300 | 169 | |
| | | | | | | 100 | 155 | |
| | | | | | | 30 | 160 | |
| | | | | | | 10 | 132 | |

The benzodiazepine derivatives inhibiting the intestinal resorption of cholesterol mentioned hereinbefore and pharmaceutically acceptable acid addition salts thereof can be used in the prevention or control of atherosclerosis, and this is also an object of the present invention. The dosage can vary within wide limits and is, of course, adjusted to the individual requirements in each particular case. In general, in the case of oral administration a daily dosage of about 10 mg to 3 g, preferably of about 100 mg to about 500 mg, should be appropriate.

The following Examples illustrate the present invention:

EXAMPLE 1

(a) 5 g (0.017 M) of 7-amino-5-(o-fluorophenyl)-1,3-dihydro-1-methyl-2H-1,4-benzodiazepin-2-one are dissolved in 60 ml of 1,2-dichloroethane under reflux. 2.5 g (0.025 M) of phosgene dissolved in ice-cold 1,2-dichloroethane are placed in a sulphonation flask. The hot dichloroethane solution of 7-amino-5-(o-fluorophenyl)-1,3-dihydro-1-methyl-2H-1,4-benzodiazepin-2-one is then added dropwise thereto while cooling with ice and stirring in such a manner that the temperature does not exceed 10° C. Subsequently, the mixture is heated at reflux for 1 hour while stirring, and the solution is then cooled to ca 10°–25° C. with ice and made basic with triethylamine. The resulting dichloroethane solution of [5-(o-fluorophenyl)-2,3-dihydro-1-methyl-2-oxo-1H-1,4-benzodiazepin-7-yl]isocyanate can be stored in a refrigerator for several hours with the exclusion of moisture. It is further processed without isolation of the isocyanate contained therein.

(b) Excess gaseous methylamine is conducted into a dichloroethane solution of [5-(o-fluorophenyl)-2,3-dihydro-1-methyl-2-oxo-1H-1,4-benzodiazepin-7-yl]isocyanate obtained as described in paragraph (a) from 5.6 g (0.019 M) of 7-amino-5-(o-fluorophenyl)-1,3-dihydro-1-methyl-2H-1,4-benzodiazepin-2-one. The mixture is then concentrated and the residue is taken up in methylene chloride/water, the methylene chloride solution is separated, washed several times with water, dried over sodium sulphate, filtered and concentrated. 1-[5-(o-Fluorophenyl)-2,3-dihydro-1-methyl-2-oxo-1H-1,4-benzodiazepin-7-yl]-3-methylurea of melting point 173° C. is crystallised from ethyl acetate.

EXAMPLE 2

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 4.2 g (0.015 M) of 7-amino-5-(o-fluorophenyl)-1,3-dihydro-1-methyl-2H-1,4-benzodiazepin-2-one, is treated with excess tert.butylamine. After concentration of the mixture, the residue is taken up in methylene chloride/water and the methylene chloride solution is washed several times with water. After drying the organic phase over sodium sulphate, the sodium sulphate is filtered off and the methylene chloride is evaporated off. The residue is purified on a silica gel column (150 g of $SiO_2$) using 40% ethyl acetate in methylene chloride as the eluting agent and crystallised from ethanol/petroleum ether. There is obtained 1-tert.butyl-3-[5-(o-fluorophenyl)-2,3-dihydro-1-methyl-2-oxo-1H-1,4-benzodiazepin-7-yl]urea which melts at 210° C. with decomposition.

EXAMPLE 3

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 5 g (0.018 M) of 7-amino-5-(o-fluorophenyl)-1,3-dihydro-1-methyl-2H-1,4-benzodiazepin-2-one, is treated with 5 ml of benzylamine and stirred at room temperature. After 0.5 hour, the solution is concentrated and the residue is taken up in a mixture of methylene chloride and 10% sodium bicarbonate solution. The organic phase is separated, washed several times with 10% sodium bicarbonate solution, dried over sodium sulphate, filtered and concentrated. Crystallisation of the residue from ethyl acetate/ether yields 1-benzyl-3-[5-(o-fluorophenyl)-2,3-dihydro-1-methyl-2-oxo-1H-1,4-benzodiazepin-7-yl]urea which melts at 174°–178° C.

EXAMPLE 4

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 6.7 g (0.024 M) of 7-amino-5-(o-fluorophenyl)-1,3-dihydro-1-methyl-2H-1,4-benzodiazepin-2-one, is treated with 8 ml of methylethylamine, the mixture is stirred at room temperature for 0.5 hour, concentrated and the residue is taken up in methylene chloride/water. The methylene chloride phase is separated, washed with water, dried over sodium sulphate, filtered and concentrated. The residue is purified on a 300 g silica gel column using ethyl acetate as the eluting agent and crystallised from ethyl acetate/ether. There is obtained 1-ethyl-3-[5-(o-fluorophenyl)-2,3-dihydro-1-methyl-2-oxo-1H-1,4-benzodiazepin-7-yl]-1-methylurea which melts at 165°–168° C.

EXAMPLE 5

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 6 g (0.021 M) of 7-amino-5-(o-fluorophenyl)-1,3-dihydro-1-methyl-2H-1,4-benzodiazepin-2-one, is treated with a solution of excess ethyleneimine in dichloroethane, the mixture is poured on to ice-water and extracted with methylene chloride. The organic phase is separated, dried with sodium sulphate, filtered and concentrated to 50 ml. The residual solution is purified quickly on a 250 g silica gel column using ethyl acetate as the eluting agent and crystallised from ethyl acetate/ether. There is obtained N-[5-(o-fluorophenyl)-2,3-dihydro-1-methyl-2-oxo-1H-1,4-benzodiazepin-7-yl]-1-aziridinecarboxamide which melts at 186°–190° C. with decomposition.

EXAMPLE 6

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 5 g (0.018 M) of 7-amino-5-(o-fluorophenyl)-1,3-dihydro-1-methyl-2H-1,4-benzodiazepin-2-one, is treated with 4.2 ml of pyrrolidine, the mixture is stirred for 20 minutes and then concentrated. The residue is purified on a 250 g silica gel column using methylene chloride/acetone (10:1) as the eluting agent and crystallised from acetone. There is obtained N-[5-(o-fluorophenyl)-2,3-dihydro-1-methyl-2-oxo-1H-1,4-benzodiazepin-7-yl]-1-pyrrolidinecarboxamide which melts at 159°–160° C.

EXAMPLE 7

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 5 g (0.018 M) of 7-amino-5-(o-fluorophenyl)-1,3-dihydro-1-methyl-2H-1,4-benzodiazepin-2-one, is treated with 5 ml of ethanolamine, the mixture is stirred for 20 minutes and then concentrated. The residue is purified on a 250 g silica gel column using methylene chloride/acetone (10:1) as the eluting agent and crystallised from acetone. There is obtained 1-[5-(o-fluorophenyl)-2,3-dihydro-1-methyl-2-oxo-1H-1,4-benzodiazepin-7-yl]-3-(2-hydroxyethyl)urea which melts at 156°–160° C. with decomposition.

EXAMPLE 8

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 4 g (0.014 M) of 7-amino-5-(o-fluorophenyl)-1,3-dihydro-1-methyl-2H-1,4-benzodiazepin-2-one, is treated with 2.2 ml of DL-alaninol in 50 ml of 1,2-dichloroethane, the mixture was stirred for 20 minutes and then concentrated. The residue is purified on a 200 g silica gel column using methylene chloride/acetone (4:1) as the eluting agent and crystallised from acetone. There is obtained rac-1-[5-(o-fluorophenyl)-2,3-dihydro-1-methyl-2-oxo-1H-1,4-benzodiazepin-7-yl]-3-(2-hydroxy-1-methylethyl)urea which melts at 165°–168° C. with decomposition.

EXAMPLE 9

(a) 80 g (0.28 M) of 7-amino-5-(o-fluorophenyl)-1,3-dihydro-1-methyl-2H-1,4-benzodiazepin-2-one are dissolved in 220 ml of concentrated hydrochloric acid and chlorine gas is slowly conducted into the solution at −10° C. for 4 hours. The mixture is slowly poured on to a mixture of ice and sodium carbonate solution (250 g of sodium carbonate dissolved in water) and extracted with methylene chloride. The extract is dried over sodium sulphate, filtered and concentrated. The residue is purified on a 1.2 kg silica gel column using methylene chloride and then methylene chloride/ethyl acetate (10:1) as the eluting agent and crystallised from ethyl acetate/ether/n-hexane. There is obtained 7-amino-6-chloro-5-(o-fluorophenyl)-1,3-dihydro-1-methyl-2H-1,4-benzodiazepin-2-one which melts at 240° C.

(b) Excess gaseous methylamine is conducted into a dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 10 g (0.031 M) of 7-amino-6-chloro-5-(o-fluorophenyl)-1,3-dihydro-1-methyl-2H-1,4-benzodiazepin-2-one, and the mixture is concentrated. The residue is dissolved in methylene chloride/water and extracted with methylene chloride. The organic phase is separated, dried with sodium sulphate, filtered and concentrated. After purification on a 500 g silica gel column using ethyl acetate as the eluting agent, the product is crystallised from ethyl acetate/ether. There is obtained 1-[6-chloro-5-(o-fluorophenyl)-2,3-dihydro-1-methyl-2-oxo-1H-1,4-benzodiazepin-7-yl]-3-methylurea which melts at 145°–160° C. with decomposition.

EXAMPLE 10

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 4 g (0.0126 M) of 7-amino-6-chloro-5-(o-fluorophenyl)-1,3-dihydro-1-methyl-2H-1,4-benzodiazepin-2-one, is treated with 2.5 ml of n-butylamine in 40 ml of 1,2-dichloroethane. The mixture is stirred at room temperature for 15 minutes, the dichloroethane solution is concentrated and the residue is purified on a 250 g silica gel column using methylene chloride and then methylene chloride/ethyl acetate (5:1) as the eluting agent. There is obtained 1-butyl-3-[6-chloro-5-(o-fluorophenyl)-2,3-dihydro-1-methyl-2-oxo-1H-1,4-benzodiazepin-7-yl]urea which melts at 196°–198° C. after recrystallisation from ether (containing very little acetone).

EXAMPLE 11

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 4 g (0.0126 M) of 7-amino-6-chloro-5-(o-fluorophenyl)-1,3-dihydro-1-methyl-2H-1,4-benzodiazepin-2-one, is treated with excess diethylamine and the mixture is concentrated. The residue is purified on a 250 g silica gel column using methylene chloride/acetone as the eluting agent and crystallised from ethyl acetate/ether. There is obtained 3-[6-chloro-5-(o-fluorophenyl)-2,3-dihydro-1-methyl-2-oxo-1H-1,4-benzodiazepin-7-yl]-1,1-diethylurea which melts at 190°–191° C.

EXAMPLE 12

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 6 g (0.019 M) of 7-amino-6-chloro-5-(o-fluorophenyl)-1,3-dihydro-1-methyl-2H-1,4-benzodiazepin-2-one, is treated with 9 ml of methylethylamine. The mixture is stirred at room temperature for 20 minutes, the dichloroethane solution is washed several times with water, dried with sodium sulphate, filtered and concentrated. The residue is purified on a 200 g silica gel column using methylene chloride/ethyl acetate (5:1) as the eluting agent and crystallised from ethyl acetate/ether. There is obtained 3-[6-chloro-5-(o-fluorophenyl)-2,3-dihydro-1-methyl-2-oxo-1H-1,4-benzodiazepin-7-yl]-1-ethyl-1-methylurea which melts at 184°–186° C.

EXAMPLE 13

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 6 g (0.019 M) of 7-amino-6-chloro-5-(o-fluorophenyl)-1,3-dihydro-1-methyl-2H-1,4-benzodiazepin-2-one, is treated with 10 ml of ethanolamine in 30 ml of 1,2-dichloroethane. The mixture is stirred for 20 minutes and then concentrated. The residue is purified on a 250 g silica gel column using methylene chloride/acetone (10:1) as the eluting agent and crystallised from ethanol/ether. There is obtained 1-[6-chloro-5-(o-fluorophenyl)-2,3-dihydro-1-methyl-2-oxo-1H-1,4-benzodiazepin-7-yl]-3-(2-hydroxyethyl)urea which melts at 150°–153° C. with decomposition.

EXAMPLE 14

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 4 g (0.012 M) of 7-amino-6-chloro-5-(o-fluorophenyl)-1,3-dihydro-1-methyl-2H-1,4-benzodiazepin-2-one, is added to a solution of 2.8 ml of 2-methylaminoethanol in 50 ml of dichloroethane, the mixture is stirred for 20 minutes and concentrated. The residue is purified on a 200 g silica gel column using methylene chloride, methylene chloride/ethyl acetate (3:1) and methylene chloride/acetone (3:1) as the eluting agent. After crystallisation from acetone, there is obtained 3-[6-chloro-5-(o-fluorophenyl)-2,3-dihydro-1-methyl-2-oxo-1H-1,4-benzodiazepin-7-yl]-1-(2-hydroxyethyl)-1-methylurea which melts at 218°–220° C.

EXAMPLE 15

A solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 4 g (0.012 M) of 7-amino-6-chloro-5-(o-fluorophenyl)-1,3-dihydro-1-methyl-2H-1,4-benzodiazepin-2-one, is added to a solution of 3 ml of isopropylamine in 50 ml of 1,2-dichloroethane, the mixture is stirred for 20 minutes and then concentrated. The residue is purified on a 260 g silica gel column using methylene chloride and then methylene chloride/ethyl acetate (5:1) as the eluting agent and crystallised from ethyl acetate/n-hexane. There is obtained 1-[6-chloro-5-(o-fluorophenyl)-2,3-dihydro-1-methyl-2-oxo-1H-1,4-benzodiazepin-7-yl]-3-isopropylurea which melts at 130°–140° C.

EXAMPLE 16

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 4 g (0.012 M) of 7-amino-6-chloro-5-(o-fluorophenyl)-1,3-dihydro-1-methyl-2H-1,4-benzodiazepin-2-one, is added to a solution of 2.5 ml of tert.butylamine in 50 ml of 1,2-dichloroethane, the mixture is stirred for 15 minutes and then concentrated. The residue is purified on a 240 g silica gel column using methylene chloride and then methylene chloride/ethyl acetate (3:1) as the eluting agent and crystallised from ether/n-hexane. There is obtained 1-[6-chloro-5-(o-fluorophenyl)-2,3-dihydro-1-methyl-2-oxo-1H-1,4-benzodiazepin-7-yl]-3-tert.butylurea which melts at 206°–208° C. with decomposition.

EXAMPLE 17

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 6 g (0.019 M) of 7-amino-6-chloro-5-(o-fluorophenyl)-1,3-dihydro-1-methyl-2H-1,4-benzodiazepin-2-one, is treated with 9 ml of N-methylpiperazine. The mixture is stirred at room temperature for 20 minutes, treated with water and extracted with methylene chloride. The organic phase is dried over sodium sulphate, filtered and concentrated. The residue is purified on a 250 g silica gel column using methylene chloride/ethanol (10:1) as the eluting agent and crystallised from ethyl acetate/ether/n-hexane. There is obtained N-[6-chloro-5-(o-fluorophenyl)-2,3-dihydro-1-methyl-2-oxo-1H-1,4-benzodiazepin-7-yl]-4-methyl-1-piperazinecarboxamide which melts at 154° C. with decomposition.

EXAMPLE 18

A dichloroethane solution of [6-chloro-5-(o-fluorophenyl)-2,3-dihydro-1-methyl-2-oxo-1H-1,4-benzodiazepin-7-yl]isocyanate, obtained in analogy to the procedure described in paragraph (a) of Example 1 from 6.66 g (0.021 M) of 7-amino-6-chloro-5-(o-fluorophenyl)-1,3-dihydro-1-methyl-2H-1,4-benzodiazepin-2-one, is treated with a solution of 6.5 g of p-chloroaniline in 50 ml of 1,2-dichloroethane. The mixture is stirred for 15 minutes, the product already crystallising out to some extent. The mixture is poured into water, cooled with ice and filtered. The insoluble product is dissolved in methylene chloride/ethanol, filtered and the filtrate is concentrated until the product begins to crystallise. There is obtained 1-[6-chloro-5-(o-fluorophenyl)-2,3-dihydro-1-methyl-2-oxo-1H-1,4-benzodiazepin-7-yl]-3-(p-chlorophenyl)urea which melts at 285° C.

EXAMPLE 19

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 8 g (0.028 M) of 7-amino-5-(o-fluorophenyl)-1,3-dihydro-1-methyl-2H-1,4-benzodiazepin-2-one, is added to a solution of 5.5 g of diethylamine in 60 ml of acetonitrile, the mixture is stirred for 20 minutes and then concentrated. The residue is purified on a 400 g silica gel column using methylene chloride/acetone (10:1) as the eluting agent and crystallised from acetone/ether. There is obtained 1,1-diethyl-3-[5-(o-fluorophenyl)-2,3-dihydro-1-methyl-2-oxo-1H-1,4-benzodiazepin-7-yl]urea which melts at 138°-139° C.

EXAMPLE 20

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 4.2 g (0.015 M) of 7-amino-5-(o-fluorophenyl)-1,3-dihydro-1-methyl-2H-1,4-benzodiazepin-2-one, is treated with 3.5 ml of thiazolidine, the mixture is stirred at room temperature for 20 minutes, treated with water and extracted with methylene chloride. The methylene chloride solution is dried over sodium sulphate, filtered and concentrated. The residue is purified on a 200 g silica gel column using methylene chloride/ethyl acetate (5:1) as the eluting agent and crystallised from methylene chloride/ethyl acetate. There is obtained N-[5-(o-fluorophenyl)-2,3-dihydro-1-methyl-2-oxo-1H-1,4-benzodiazepin-7-yl]-3-thiazolidinecarboxamide which melts at 185° C. with decomposition.

EXAMPLE 21

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 4 g (0.014 M) of 7-amino-5-(o-fluorophenyl)-1,3-dihydro-1-methyl-2H-1,4-benzodiazepin-2-one, is added to a solution of 3 ml of 2-methylaminoethanol in 50 ml of 1,2-dichloroethane, the mixture is stirred for 15 minutes and then concentrated. The residue is purified on a 200 g silica gel column using methylene chloride and then methylene chloride/acetone (10:1) as the eluting agent and crystallised from acetone. There is obtained 3-[5-(o-fluorophenyl)-2,3-dihydro-1-methyl-2-oxo-1H-1,4-benzodiazepin-7-yl]-1-(2-hydroxyethyl)-1-methylurea which melts at 196°-198° C. with decomposition.

EXAMPLE 22

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 12.5 g (0.044 M) of 7-amino-5-(o-fluorophenyl)-1,3-dihydro-1-methyl-2H-1,4-benzodiazepin-2-one, is reacted with a solution of 8 g of 3-amino-1-propanol in 100 ml of 1,2-dichloroethane. The mixture is stirred for 15 minutes, concentrated and the residue is purified on a 270 g silica gel column using acetone as the eluting agent. After crystallisation from acetone, there is obtained 1-[5-(o-fluorophenyl)-2,3-dihydro-1-methyl-2-oxo-1H-1,4-benzodiazepin-7-yl]-3-(3-hydroxypropyl)urea which melts at 118°-119° C. with decomposition.

EXAMPLE 23

A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 4 g (0.014 M) of 7-amino-5-(o-fluorophenyl)-1,3-dihydro-1-methyl-2H-1,4-benzodiazepin-2-one, is added to a solution of 2.5 ml of 2-amino-2-methyl-1-propanol in 50 ml of 1,2-dichloroethane, the mixture is stirred at room temperature for 15 minutes and then concentrated. The residue is purified on a 200 g silica gel column using methylene chloride and then methylene chloride/acetone (1:1) as the eluting agent. After crystallisation from acetone/ether, there is obtained 1-[5-(o-fluorophenyl)-2,3-dihydro-1-methyl-2-oxo-1H-1,4-benzodiazepin-7-yl]-3-(2-hydroxy-1,1-dimethylethyl)urea which melts at 162°-176° C. with decomposition.

EXAMPLE 24

A dichloroethane solution of [5-(o-fluorophenyl)-2,3-dihydro-1-methyl-2-oxo-1H-1,4-benzodiazepin-7-yl]isocyanate, prepared as described in paragraph (a) of Example 1 from 12.5 g (0.044 M) of 7-amino-5-(o-fluorophenyl)-1,3-dihydro-1-methyl-2H-1,4-benzodiazepin-2-one, is added to a solution of 8 g of 1-amino-2-propanol in 100 ml of 1,2-dichloroethane, the mixture is stirred at room temperature for 15 minutes and then concentrated. The residue is purified on a 300 g silica gel column using methylene chloride and then acetone as the eluting agent. This operation is repeated once using ethyl acetate as the eluting agent. After crystallisation from ethyl acetate, there is obtained rac-1-[5-(o-fluorophenyl)-2,3-dihydro-1-methyl-2-oxo-1H-1,4-benzodiazepin-7-yl]-3-(2-hydroxypropyl)urea which melts at 149°-151° C. with decomposition.

EXAMPLE 25

(a) 50 g of carbobenzoxy-DL-alanine are dissolved in 400 ml of absolute tetrahydrofuran, treated dropwise while cooling with ice with 30 g of thionyl chloride and stirred for 40 minutes, a suspension of 50 g of 2-amino-5-nitro-2'-fluorobenzophenone in 200 ml of absolute tetrahydrofuran then being rapidly added dropwise. Subsequently, the mixture is stirred at room temperature for 18 hours, the solution is concentrated and the residue is treated with ice and 10% sodium bicarbonate solution. The mixture is extracted with methylene chloride, the organic solution is dried with sodium sulphate, filtered and concentrated. The residue is crystallised from ethanol and yields rac-benzyl-{1-[[2-(o-fluorobenzoyl)-4-nitrophenyl]carbamoyl]ethyl}carbamate which is further processed directly as the crude product.

(b) 70 g (0.15 M) of the foregoing crude product are treated with 200 ml of 30-33% hydrogen bromide solution in glacial acetic acid, the mixture is stirred at room temperature for 0.5 hour, concentrated, treated with water and extracted 2-3 times with ether. The aqueous solution is cooled in ice, neutralised with solid sodium bicarbonate and extracted with methylene chloride.

The methylene chloride extract is dried with sodium sulphate, filtered and concentrated. The residue is treated with 40 ml of glacial acetic acid and 400 ml of toluene. The mixture is heated to reflux for 20 minutes and evaporated. The residual oil is dissolved in methylene chloride, washed with saturated sodium bicarbonate solution, dried over sodium sulphate, filtered and concentrated. After crystallisation from ethyl acetate/petroleum ether, there is obtained rac-5-(o-fluorophenyl)-1,3-dihydro-3-methyl-7-nitro-2H-1,4-benzodiazepin-2-one which melts at 230°–234° C.

(c) 95 g (0.30 M) of rac-5-(o-fluorophenyl)-1,3-dihydro-3-methyl-7-nitro-2H-1,4-benzodiazepin-2-one are dissolved in 1 liter of absolute acetone and treated with 60 g of powdered potassium carbonate and 43 g of dimethyl sulphate. The mixture is stirred at room temperature for 4 hours and left to stand in a refrigerator for 48 hours. The mixture is then concentrated, treated with ice-water and extracted several times with methylene chloride. The organic solution is dried over sodium sulphate, filtered and concentrated. The residue is crystallised from ethyl acetate/petroleum ether, there being obtained rac-5-(o-fluorophenyl)-1,3-dihydro-1,3-dimethyl-7-nitro-2H-1,4-benzodiazepin-2-one which melts at 154°–156° C.

(d) 85 g (0.26 M) of rac-5-(o-fluorophenyl)-1,3-dihydro-1,3-dimethyl-7-nitro-2H-1,4-benzodiazepin-2-one are dissolved in 700 ml of concentrated hydrochloric acid and treated slowly with 180 g of stannous chloride. After about 15 minutes, the mixture is cooled with ice and then concentrated on a rotary evaporator. The residue is dissolved in ice-water, slowly made alkaline with 200 g of sodium carbonate in 1 liter of water and extracted several times with methylene chloride. The organic solution is dried over sodium sulphate, filtered and concentrated. The residue is crystallised from ethyl acetate and there is obtained rac-7-amino-5-(o-fluorophenyl)-1,3-dihydro-1,3-dimethyl-2H-1,4-benzodiazepin-2-one which melts at 178°–180° C.

(e) A dichloroethane solution of rac-[5-(o-fluorophenyl)-2,3-dihydro-1,3-dimethyl-2-oxo-1H-1,4-benzodiazepin-7-yl]isocyanate, obtained in analogy to the procedure described in paragraph (a) of Example 1 from 5 g (0.017 M) of rac-7-amino-5-(o-fluorophenyl)-1,3-dihydro-1,3-dimethyl-2H-1,4-benzodiazepin-2-one, is treated rapidly while cooling with ice with excess gaseous methylamine and the mixture is stirred at room temperature for 15 minutes. The mixture is treated with water and extracted with methylene chloride. The organic phase is dried over sodium sulphate, filtered and concentrated. The residue is purified on a 250 g silica gel column using methylene chloride/ethyl acetate and then ethyl acetate as the eluting agent and crystallised from ether/n-hexane. There is obtained rac-1-[5-(o-fluorophenyl)-2,3-dihydro-1,3-dihydro-1,3-dimethyl-2-oxo-1H-1,4-benzodiazepin-7-yl]-3-methylurea which melts at 109°–111° C. with decomposition.

EXAMPLE 26

(a) 120 g of carbobenzoxy-L-alanine are dissolved in 800 ml of absolute tetrahydrofuran, treated dropwise while cooling with ice with 70 g of thionyl chloride and stirred for 40 minutes while cooling with ice. There is then rapidly added dropwise thereto a suspension of 100 g (0.38 M) of 2-amino-5-nitro-2'-fluorobenzophenone in 400 ml of absolute tetrahydrofuran and the mixture is stirred at room temperature for 24 hours. The solution obtained is concentrated and the residue is treated with ice and 10% sodium bicarbonate solution and extracted with methylene chloride. The organic solution is dried over sodium sulphate, filtered and concentrated. The residue is dissolved in a small amount of methylene chloride and treated with ether. There is obtained (S)-benzyl-{1-[[2-(o-fluorobenzoyl)-4-nitrophenyl]carbamoyl]ethyl}carbamate. A further recrystallisation from methylene chloride/ether yields a product which melts at 158°–160° C. and shows a rotation of $[\alpha]_{25}^D = -23.4°$ (in methylene chloride; 1%). The mother liquors are purified on a 600 g silica gel column using methylene chloride as the eluting agent, an additional amount of the aforementioned product being obtained.

(b) 110 g (0.24 M) of (S)-benzyl-{1-[[2-(o-fluorobenzoyl)-4-nitrophenyl]carbamoyl]ethyl}carbamate are dissolved in 400 ml of 30–33% hydrogen bromide solution in glacial acetic acid. 30 ml of methylene chloride are added thereto, the mixture is stirred at room temperature for 45 minutes, concentrated, treated with water and extracted 2–3 times with ether. The aqueous solution is cooled in ice, neutralised with solid sodium bicarbonate, extracted with methylene chloride, dried over sodium sulphate, filtered and concentrated. The residue is treated with 50 ml of glacial acetic acid and 500 ml of toluene. The mixture is heated to reflux for 15 to 20 minutes and evaporated. The residual oil is dissolved in methylene chloride and the solution obtained is washed with saturated sodium bicarbonate solution, dried over sodium sulphate, filtered and concentrated. The residue is dissolved in 400 ml of benzene and seeded with rac-5-(o-fluorophenyl)-1,3-dihydro-3-methyl-7-nitro-2H-1,4-benzodiazepin-2-one. The mixture is left to stand at room temperature overnight, 2 g of racemate crystallising out. The mother liquor is concentrated and treated with ether. By crystallisation from ether there is obtained (S)-5-(o-fluorophenyl)-1,3-dihydro-3-methyl-7-nitro-2H-1,4-benzodiazepin-2-one which melts at 130°–134° C.; $[\alpha]_{25}^D = +377.2°$ (in methylene chloride; 1%).

(c) 57.5 g (0.18 M) of (S)-5-(o-fluorophenyl)-1,3-dihydro-3-methyl-7-nitro-2H-1,4-benzodiazepin-2-one are dissolved in 600 ml of absolute acetone. The solution is treated with 48 g of powdered potassium carbonate and 21 ml of methyl iodide and stirred at room temperature for 5 hours. The mixture is concentrated and the residue is treated with ice-water and extracted several times with methylene chloride. The methylene chloride solution is washed with water, dried over sodium sulphate, filtered and concentrated. The residue is crystallised from ether/petroleum ether and there is obtained (S)-5-(o-fluorophenyl)-1,3-dihydro-1,3-dimethyl-7-nitro-2H-1,4-benzodiazepin-2-one which melts at 118°–126° C. with decomposition; $[\alpha]_{25}^D = +563.1°$ (in methylene chloride; 1%).

(d) 1 g of (S)-5-(o-fluorophenyl)-1,3-dihydro-1,3-dimethyl-7-nitro-2H-1,4-benzodiazepin-2-one is introduced portionwise into 10 ml of concentrated hydrochloric acid while cooling with ice at 0° C. The solution obtained is treated slowly at 0° C. with 2 g of stannous chloride, stirred for 30 minutes while cooling with ice, poured into ice/sodium bicarbonate solution and extracted several times with methylene chloride. The organic phase is dried over sodium sulphate, filtered and concentrated. After crystallisation from ether, there is obtained (S)-7-amino-5-(o-fluorophenyl)-1,3-dihydro-1,3-dimethyl-2H-1,4-benzodiazepin-2-one which crystallises with 1 mol of ether; melting point 00°–110° C. (with decomposition); $[\alpha]_{25}^D = +77.1°$ (in methylene chloride; 1%).

(e) 4 g (0.011 M) of (S)-7-amino-5-(o-fluorophenyl)-1,3-dihydro-1,3-dimethyl-2H-1,4-benzodiazepin-2-one are dissolved in 35 ml of ice-cold concentrated hydrochloric acid at −10° C. and chlorine gas is conducted in it −10° C. for 1 hour. The mixture is concentrated at 0°–5° C. using a high vacuum cooling trap and a soda lime tower under a high vacuum (1–2 mmHg). The residue is made alkaline with a mixture of ice and 10% sodium bicarbonate solution. The mixture is extracted with methylene chloride and the extract is dried over sodium sulphate, filtered and concentrated. The remaining oil is purified on a 300 g silica gel column using methylene chloride and then methylene chloride/ethyl acetate (20:1) as the eluting agent. This operation is repeated once on a 120 g silica gel column using methylene chloride and then methylene chloride/ethyl acetate (20:1) as the eluting agent. After crystallisation from ethyl acetate/ether, there is obtained (S)-7-amino-6-chloro-5-(o-fluorophenyl)-1,3-dihydro-1,3-dimethyl-2H-1,4-benzodiazepin-2-one which melts at 222°–226° C.; $[\alpha]_{25}^D = +92°$ (in methylene chloride; 0.5%).

(f) A solution of 2 g of phosgene in 20 ml of ice-cold 1,2-dichloroethane is placed in a sulphonation flask. There is added dropwise thereto a solution of 4 g (0.012 M) of (S)-7-amino-6-chloro-5-(o-fluorophenyl)-1,3-dihydro-1,3-dimethyl-2H-1,4-benzodiazepin-2-one in 40 ml of 1,2-dichloroethane while cooling with ice and stirring in such a manner that the temperature does not exceed 10° C. The mixture is then stirred at room temperature for 45 minutes. The resulting solution of (S)-[6-chloro-5-(o-fluorophenyl)-2,3-dihydro-1,3-dimethyl-2-oxo-1H-1,4-benzodiazepin-7-yl]isocyanate is cooled with ice and slowly made alkaline with 6 ml of triethylamine. A solution of 2 ml of 2-aminoethanol in 20 ml of 1,2-dichloroethane is treated with the foregoing prepared solution, the mixture is stirred at room temperature for 30 minutes and then concentrated. The residue is purified on a 300 g silica gel column using methylene chloride and then methylene chloride/ethanol (20:1) as the eluting agent and crystallised from a small amount of ethyl acetate/n-hexane. There is obtained (S)-1-[6-chloro-5-(o-fluorophenyl)-2,3-dihydro-1,3-dimethyl-2-oxo-1H-1,4-benzodiazepin-7-yl]-3-(2-hydroxyethyl)urea which melts above 147° C. with decomposition; $[\alpha]_{25}^D = +192.2°$ (in dioxan; 1%).

EXAMPLE 27

(a) From 120 g of carbobenzoxy-D-alanine and 100 g (0.38 M) of 2-amino-5-nitro-2'-fluorobenzophenone there is obtained in analogy to the procedure described in paragraph (a) of Example 26 (R)-benzyl-{1-[[2-(o-fluorobenzoyl)-4-nitrophenyl]carbamoyl]ethyl}carbamate. This product, crystallised from methylene chloride/ether, melts at 158°–160° C.; $[\alpha]_{25}^D = +16.5°$.

(b) From 90 g (0.19 M) of (R)-benzyl-}1-[[2-(o-fluorobenzoyl)-4-nitrophenyl]carbamoyl]ethyl}carbamate there is obtained in analogy to the procedure described in paragraph (b) of Example 26 (R)-5-(o-fluorophenyl)-1,3-dihydro-3-methyl-7-nitro-2H-1,4-benzodiazepin-2-one. This product, crystallised from ether/n-hexane, melts at 130°–140° C.; $[\alpha]_{25}^D = -361.9°$ (in methylene chloride; 1%).

(c) From 44.6 g (0.14 M) of (R)-5-(o-fluorophenyl)-1,3-dihydro-3-methyl-7-nitro-2H-1,4-benzodiazepin-2-one there is obtained in analogy to the procedure described in paragraph (c) of Example 26 (R)-5-(o-fluorophenyl)-1,3-dihydro-1,3-dimethyl-7-nitro-2H-1,4-benzodiazepin-2-one. This product, crystallised from ether/hexane, melts at 120° C.; $[\alpha]_{25}^D = -540.7°$ (in methylene chloride; 1%).

(d) From 5 g (0.015 M) of (R)-5-(o-fluorophenyl)-1,3-dihydro-1,3-dimethyl-7-nitro-2H-1,4-benzodiazepin-2-one there is obtained in analogy to the procedure described in paragraph (d) of Example 26 7-amino-5-(o-fluorophenyl)-1,3-dihydro-1,3-dimethyl-2H-1,4-benzodiazepin-2-one. This product, crystallised from ether/petroleum ether, melts at 95°–110° C. with decomposition (crystallization occurs with 1 mol of ether); $[\alpha]_{25}^D = -78.4°$ (in methylene chloride; 1%).

(e) From 10 g (0.027 M) of (R)-7-amino-5-(o-fluorophenyl)-1,3-dihydro-1,3-dimethyl-2H-1,4-benzodiazepin-2-one there is obtained in analogy to the procedure described in paragraph (e) of Example 26 (R)-7-amino-6-chloro-5-(o-fluorophenyl)-1,3-dihydro-1,3-dimethyl-2H-1,4-benzodiazepin-2-one which is recrystallized from ether and then melts at 224°–226° C.; $[\alpha]_{25}^D = -95.4°$ (in dioxan; 1%).

(f) From 4 g (0.012 M) of (R)-7-amino-6-chloro-5-(o-fluorophenyl)-1,3-dihydro-1,3-dimethyl-2H-1,4-benzodiazepin-2-one there is obtained in analogy to the procedure described in paragraph (f) of Example 26 (R)-1-[6-chloro-5-(o-fluorophenyl)-2,3-dihydro-1,3-dimethyl-2-oxo-1H-1,4-benzodiazepin-7-yl]-3-(2-hydroxyethyl)urea which melts above 100° C. with decomposition (recrystallised from a small amount of ethyl acetate/n-hexane); $[\alpha]_{25}^D = -188.8°$ (in dioxan; 1%).

EXAMPLE 28

(a) From 56 g of carbobenzoxy-DL-α-aminobutyric acid and 54 g (0.21 M) of 2-amino-5-nitro-2'-fluorobenzophenone there is obtained in analogy to the procedure described in paragraph (a) of Example 25 benzyl-rac-{1-[[(2-(o-fluorobenzoyL)-4-nitrophenyl]carbamoyl]propyl}carbamate which is crystallised from ether and then melts at 135°–136° C.

(b) From 60 g (0.125 M) of benzyl rac-{1-[[2-(o-fluorobenzoyl)-4-nitrophenyl]carbamoyl]propyl}carbamate there is obtained in analogy to the procedure described in paragraph. (b) of Example 25 rac-3-ethyl-5-(o-fluorophenyl)-1,3-dihydro-7-nitro-2H-1,4-benzodiazepin-2-one which is crystallised from methylene chloride and then melts at 260° C. with decomposition.

(c) 30 g (0.092 M) of rac-3-ethyl-5-(o-fluorophenyl)-1,3-dihydro-7-nitro-2H-1,4-benzodiazepin-2-one are dissolved in 200 ml of absolute acetone, treated with 16 g of powdered potassium carbonate and 8 ml of methyl iodide and the mixture is stirred at room temperature. After 1 hour, a further 4 ml of methyl iodide are added and the mixture is stirred for a further 2.5 hours. The undissolved inorganic salts are filtered off under suction and the solution is concentrated. The residue is treated with water, the mixture is extracted with methylene chloride and the extract is dried with sodium sulphate, filtered and concentrated. After crystallisation from ethyl acetate/petroleum ether, there is obtained rac-3-ethyl-5-(o-fluorophenyl)-1,3-dihydro-1-methyl-7-nitro-2H-1,4-benzodiazepin-2-one which melts at 175°–176° C.

(d) From 4 g (0.012 M) of rac-3-ethyl-5-(o-fluorophenyl)-1,3-dihydro-1-methyl-7-nitro-2H-1,4-benzodiazepin-2-one there is obtained in analogy to the procedure described in paragraph (d) of Example 25 rac-7-amino-3-ethyl-5-(o-fluorophenyl)-1,3-dihydro-1- methyl-2H-1,4-benzodiazepin-2-one which is crystallised from ethyl acetate and then melts at 185°–186° C.

(e) 9.3 g (0.03 M) of rac-7-amino-3-ethyl-5-(o-fluorophenyl)-1,3-dihydro-1-methyl-2H-1,4-benzodiazepin-2-one are dissolved in 80 ml of glacial acetic acid. The solution is cooled to 10° C., treated dropwise with 5 g (1.62 ml) of bromine, stirred at 10° C. for a further 10 minutes after the addition of bromine and then concentrated. The residue is treated with a mixture of ice and 10% sodium bicarbonate solution, extracted with methylene chloride and the extract is dried over sodium sulphate, filtered and concentrated. The residual oil is purified on a 200 g silica gel column with methylene chloride/ethyl acetate (10:1) and crystallised from ether. There is obtained rac-7-amino-3-ethyl-6-bromo-5-(o-fluorophenyl)-1,3-dihydro-1-methyl-2H-1,4-benzodiazepin-2-one which melts at 248° C.

(f) A solution of rac-[7-amino-3-ethyl-6-bromo-5-(o-fluorophenyl)-2,3-dihydro-1-methyl-2-oxo-1H-1,4-benzodiazepin-7-yl]isocyanate, obtained from 8.5 g (0.022 M) of rac-7-amino-3-ethyl-6-bromo-(o-fluorophenyl)-1,3-dihydro-1-methyl-2H-1,4-benzodiazepin-2-one in analogy to the procedure described in paragraph (a) of Example 1, is added to a solution of 8.5 ml of 2-aminoethanol in 40 ml of 1,2-dichloroethane, the mixture is stirred for 15 minutes and then concentrated. The residue is purified on a 400 g silica gel column using methylene chloride/acetone as the eluting agent and crystallised from acetone/ether. There is obtained rac-1-[3-ethyl-6-bromo-5-(o-fluorophenyl)-2,3-dihydro-1-methyl-2-oxo-1H-1,4-benzodiazepin-7-yl]-3-(2-hydroxyethyl)urea which melts at 218°–222° C.

EXAMPLE 29

(a) 13 g (0.042 M) of rac-7-amino-3-ethyl-5-(o-fluorophenyl)-1,3-dihydro-1-methyl-2H-1,4-benzodiazepin-2-one are dissolved in 70 ml of concentrated hydrochloric acid at −10° C. and chlorine gas is then conducted in at −10° C. until the starting material can no longer be detected by thin-layer chromatography. The mixture is neutralised slowly with a mixture of ice and 10% sodium carbonate solution and the mixture is extracted several times with methylene chloride. The organic solution is washed with water, dried over sodium sulphate, filtered and concentrated. The residue is purified on a 300 g silica gel column with methylene chloride/ethyl acetate (10:1) and crystallised from ethanol. There is obtained rac-7-amino-3-ethyl-6-chloro-5-(o-fluorophenyl)-1,3-dihydro-1-methyl-2H-1,4-benzodiazepin-2one which melts at 250° C.

(b) A solution of [3-ethyl-6-chloro-5-(o-fluorophenyl)-2,3-dihydro-1-methyl-2-oxo-1H-1,4-benzodiazepin-7-yl]isocyanate, obtained from 3.4 g (0.01 M) of rac-7-amino-3-ethyl-6-chloro-5-(o-fluorophenyl)-1,3-dihydro-1-methyl-2H-1,4-benzodiazepin-2-one in analogy to the procedure described in paragraph (a) of Example 1, is added to a solution of 2 ml of 2-aminoethanol in 50 ml of 1,2-dichloroethane, the mixture is stirred at room temperature for 15 minutes and then concentrated. The residue is purified on a 200 g silica gel column using methylene chloride/ethyl acetate (1:1) and then ethyl acetate as the eluting agent and crystallised from acetone/ether. There is obtained rac-1-[3-ethyl-6-chloro-5-(o-fluorophenyl)-2,3-dihydro-1-methyl-2-oxo-1H-1,4-benzodiazepin-7yl]-3-(2-hydroxyethyl)urea which melts at 243°–244° C.

EXAMPLE 30

(a) 19.7 g of N-carbobenzoxy-DL-norleucine are dissolved in 200 ml of absolute tetrahydrofuran, the solution is treated dropwise while cooling with ice with 10 g of thionyl chloride and then stirred for 1 hour. To this solution there is rapidly added dropwise a solution of 17 g (0.065 M) of 2-amino-5-nitro-2'-fluorobenzophenone in 130 ml of absolute tetrahydrofuran and the mixture is then stirred at room temperature for 60 hours. The solution is concentrtated and the residue is treated with ice and 10% sodium bicarbonate solution and extracted with methylene chloride. The organic solution is dried with sodium sulphate, filtered and concentrated. The residue is purified on a 450 g silica gel column using methylene chloride as the eluting agent and crystallised from ethanol. There is obtained benzyl-rac-{1-[[2-(o-fluorobenzoyl)-4-nitrophenyl]carbamoyl]butyl}carbamate which melts at 148°–150° C.

(b) From 24.5 g (0.05 M) of benzyl-rac-{1-[[2-(o-fluorobenzoyl)-4-nitrophenyl]carbamoyl]butyl}carbamate there is obtained in analogy to the procedure described in paragraph (b) of Example 25 rac-5-(o-fluorophenyl)-1,3-dihydro-7-nitro-3-propyl-2H-1,4-benzodiazepin-2-one which is crystallised from methylene chloride/ethanol and then melts at 245°–246° C.

(c) From 13.6 g (0.04 M) of rac-5-(o-fluorophenyl)-1,3-dihydro-7-nitro-3-propyl-2H-1,4-benzodiazepin-2-one there is obtained in analogy to the procedure described in paragraph (c) of Example 28 rac-5-(o-fluorophenyl)-1,3-dihydro-1-methyl-7-nitro-3-propyl-2H-1,4-benzodiazepin-2-one which is crystallised from ether/petroleum ether and then melts at 128°–130° C.

(d) From 11.7 g (0.033 M) of rac-5-(o-fluorophenyl)-1,3-dihydro-1-methyl-7-nitro-3-propyl-2H-1,4-benzodiazepin-2-one there is obtained in analogy to the procedure described in paragraph (d) of Example 25 rac-7-amino-5-(o-fluorophenyl)-1,3-dihydro-1-methyl-3-propyl-2H-1,4-benzodiazepin-2-one which is crystallised from ether and then melts at 112°–116° C.

(e) A solution of rac-[5-(o-fluorophenyl)-2,3-dihydro-1-methyl-2-oxo-3-propyl-1H-1,4-benzodiazepin-7-yl]isocyanate, obtained from 4 g (0.012 M) of rac-7-amino-5-(o-fluorophenyl)-1,3-dihydro-1-methyl-3-propyl-2H-1,4-benzodiazepin-2-one in analogy to the procedure described in paragraph (a) of Example 1, is added to a solution of 2 ml of 2-aminoethanol in 50 ml of 1,2-dichloroethane. The mixture is stirred at room temperature for 15 minutes and then concentrated. The residue is purified on a 250 g silica gel column with methylene chloride and then with methylene chloride/ethanol (20:1) and crystallised from ethyl acetate/n-hexane. There is obtained rac-1-[5-(o-fluorophenyl)-2,3-dihydro-1-methyl-2-oxo-3-propyl-1H-1,4-benzodiazepin-7-yl]-3-(2-hydroxyethyl)urea which melts at 105°–110° C. with decomposition.

EXAMPLE 31

(a) From 94 g of N-carbobenzoxy-DL-α-aminobutyric acid and 93 g (0.34 M) of 2-amino-5-nitro-2'-chlorobenzophenone there is obtained in analogy to the procedure described in paragraph (a) of Example 30 benzyl-rac-{1-[[2-(o-chlorobenzoyl)-4-nitrophenyl]carbamoyl]propyl}carbamate which is crystallised from ether/n-hexane and then melts at 142° C.

(b) From 70 g (0.14 M) of benzyl-rac-{1-[[2-(o-chlorobenzoyl)-4-nitrophenyl]carbamoyl]propyl}carbamate there is obtained in analogy to the procedure described in paragraph (b) of Example 25 rac-3-ethyl-5-(o-chlorophenyl)-1,3-dihydro-7-nitro-2H-1,4-benzodiazepin-2-one which is crystallised from methylene chloride/ether and then melts at 242°–243° C.

(c) From 46.9 g (0.14 M) of rac-3-ethyl-5-(o-chlorophenyl)-1,3-dihydro-7-nitro-2H-1,4-benzodiazepin-2-one there is obtained in analogy to the procedure described in paragraph (c) of Example 28, but after stirring for 16 hours at room temperature and then for 3 hours at 40° C., rac-3-ethyl-5-(o-chlorophenyl)-1,3-dihydro-1-methyl-7-nitro-2H-1,4-benzodiazepin-2-one. This product, recrystallised from ethyl acetate/ether, melts at 161°–162° C.

(d) 7.7 g (0.021 M) of rac-3-ethyl-5-(o-chlorophenyl)-1,3-dihydro-1-methyl-7-nitro-2H-1,4-benzodiazepin-2-one are dissolved in 85 ml of concentrated hydrochloric acid, treated with 18 g of stannous chloride and stirred at room temperature for 30 minutes. The mixture is poured into a mixture of ice and sodium carbonate solution, extracted with methylene chloride and the extract is dried over sodium sulphate, filtered and concentrated. After crystallisation from ethyl acetate/ether there is obtained rac-7-amino-3-ethyl-5-(o-chlorophenyl)-1,3-dihydro-1-methyl-2H-1,4-benzodiazepin-2-one which melts at 198°–199° C.

(e) 9.6 g (0.029 M) of rac-7-amino-3-ethyl-5-(o-chlorophenyl)-1,3-dihydro-1-methyl-2H-1,4-benzodiazepin-2-one dissolved in 50 ml of concentrated aqueous hydrobromic acid are treated slowly at between 0°–5° C. with 5.2 g (1.65 ml) of bromine and the mixture is stirred at 0° C. for 1 hour. The mixture is then poured on to a mixture of ice and sodium carbonate solution, extracted with methylene chloride and the extract is dried over sodium sulphate, filtered and concentrated. After crystallisation from methylene chloride/ether/petroleum ether, there is obtained rac-7-amino-3-ethyl-6-bromo-5-(o-chlorophenyl)-1,3-dihydro-1-methyl-2H-1,4-benzodiazepin-2-one which melts at 251° C. with decomposition.

(f) A solution of rac-[3-ethyl-6-bromo-5-(o-chlorophenyl)-1-methyl-2-oxo-2,3-dihydro-1H-1,4-benzodiazepin-7-yl]isocyanate, obtained from 4 g (0.01 M) of rac-7-amino-3-ethyl-6-bromo-5-(o-chlorophenyl)-1,3-dihydro-1-methyl-2H-1,4-benzodiazepin-2-one in analogy to the procedure described in paragraph (a) of Example 1, is added to a solution of 2.5 ml of 2-aminoethanol in 50 ml of 1,2-dichloroethane. The mixture is stirred at room temperature for 15 minutes and then concentrated. The residue is purified on a 250 g silica gel column using methylene chloride and then methylene chloride/acetone (10:1) as the eluting agent and crystallised from acetone. There is obtained rac-1-[3-ethyl-6-bromo-5-(o-chlorophenyl)-2,3-dihydro-1-methyl-2-oxo-1H-1,4-benzodiazepin-7-yl]-3-(2-hydroxyethyl)urea which melts at 236°–237° C.

EXAMPLE 32

4.2 g (0.015 M) of 7-amino-5-(o-fluorophenyl)-1,3-dihydro-1-methyl-2H-1,4-benzodiazepin-2-one are suspended in 60 ml of absolute methylene chloride, treated with 2.1 g of powdered potassium carbonate and 1.6 ml of dimethylcarbamoyl chloride and stirred at 20° C. for 14 days. The mixture is then poured on to a mixture of ice and water, extracted with methylene chloride and the organic phase is washed 2–3 times with water, dried with sodium sulphate, filtered and concentrated. The residue is purified on a 200 g silica gel column using ethyl acetate as the eluting agent and crystallised from ethanol/petroleum ether. There is obtained 3-[5-(o-fluorophenyl)-2,3-dihydro-1-methyl-2-oxo-1H-1,4-benzodiazepin-7-yl]-1,1-dimethylurea which crystallises with 0.5 mol of ethanol and melts at 97° C. with decomposition.

EXAMPLE 33

4.2 g (0.015 M) of 7-amino-5-(o-fluorophenyl)-1,3-dihydro-1-methyl-2H-1,4-benzodiazepin-2-one are suspended in 50 ml of absolute methylene chloride, treated with 2.5 ml of p-methoxyphenylisocyanate and 2 drops of triethylamine and stirred at room temperature overnight. The mixture is concentrated partially and treated with ethyl acetate, 1-[5-(o-fluorophenyl)-2,3-dihydro-1-methyl-2-oxo-1H-1,4-benzodiazepin-7-yl]-3-(p-methoxyphenyl)urea crystallising out. This product melts at 240° C. with decomposition.

EXAMPLE 34

5 g (0.016 M) of 7-amino-6-chloro-5-(o-fluorophenyl)-1,3-dihydro-1-methyl-2H-1,4-benzodiazepin-2-one are heated at reflux with 15 ml of ethylisocyanate under nitrogen for 7 hours. The mixture is poured on to methanol/ice-water and extracted with methylene chloride. The organic phase is separated, dried with sodium sulphate, filtered and concentrated. The residue is purified on a 300 g silica gel column using ethyl acetate as the eluting agent and crystallised from ethyl acetate/ether. There is obtained 1-[6-chloro-5-(o-fluorophenyl)-2,3-dihydro-1-methyl-2-oxo-1H-1,4-benzodiazepin-7-yl]-3-ethylurea which melts at 155°–160° C. with decomposition.

EXAMPLE 35

5 g (0.018 M) of 7-amino-1,3-dihydro-1-methyl-5-(o-fluorophenyl)-2H-1,4-benzodiazepin-2-one are heated at reflux for 5 hours with 15 ml of isopropylisocyanate and a catalytic amount of triethylamine. The mixture is left to stand at room temperature for 2.5 days, the product crystallising out partially. The solvent is concentrated partially, cooled with ice and the crystallised product is filtered off. After recrystallisation from methylene chloride/ethyl acetate, there is obtained 1-[5-(o-fluorophenyl)-2,3-dihydro-1-methyl-2-oxo-1H-1,4-benzodiazepin-7-yl]-3-isopropylurea which melts at 185°–188° C. with decomposition.

EXAMPLE 36

11.1 g (0.03 M) of 1-[5-(o-fluorophenyl)-2,3-dihydro-1-methyl-2-oxo-1H-1,4-benzodiazepin-7-yl]-3-(2-hydroxyethyl)urea are stirred at room temperature for 18 hours in 150 ml of acetonitrile with 3.9 ml of acetyl chloride and 9 g of powdered potassium carbonate. The mixture is concentrated on a rotary evaporator and the residue is purified on a 500 g silica gel column using methylene chloride/ethanol as the eluting agent. After crystallisation from ethyl acetate, there is obtained 2-[3-[5-(o-fluorophenyl)-2,3-dihydro-1-methyl-2-oxo-1H-1,4-benzodiazepin-7-yl]ureido]ethyl acetate which melts at 196°–198° C.

EXAMPLE 37

(a) 45 g of carbobenzoxy-glycine dissolved in 1 liter of absolute tetrahydrofuran are treated dropwise while cooling with ice with 20 ml of thionyl chloride and stirred for 1 hour while cooling with ice. There is then rapidly added dropwise thereto a suspension of 50 g of 2-amino-5-nitro-2'-fluorobenzophenone in 200 ml of absolute tetrahydrofuran and the mixture is stirred at room temperature for 18 hours. The solution obtained is concentrated and the residue is treated with ice and 10% sodium bicarbonate solution and extracted with methylene chloride. The organic solution is dried over sodium sulphate, filtered and concentrated. The residue is dissolved in a small amount of hot ethyl acetate, concentrated partially and treated with ether. Benzyl{[[2-(o-fluorobenozyl)-4-nitrophenyl]carbamoyl]methyl}-carbamate is obtained. The mother liquors are purified on a 100 g silica gel column using methylene chloride as the eluting agent, an additional amount of the aforementioned product being obtained.

(b) 4.5 g (0.01 M) of benzyl{[[2-(o-fluorobenzoyl)-4-nitrophenyl]carbamoyl]methyl}carbamate dissolved in 50 ml of absolute acetone are treated with 4.5 g of powdered potassium carbonate and 2 ml of methyl iodide and the mixture is stirred at room temperature for 6 days. The insoluble material is then filtered off and washed with acetone. The combined acetone solutions are concentrated. The residue is purified on a 250 g silica gel column using methylene chloride/ethyl acetate (10:1) and then methylene chloride/ethyl acetate (5:1) as the eluting agent and crystallised from ether/petroleum ether. There is obtained benzyl{[[2-(o-fluorobenzoyl)-4-nitrophenyl]methylcarbamoyl]methyl}carbamate which melts at 112° C.

(c) 10.5 g (0.0225 M) of benzyl{[[2-(o-fluorobenzoyl)-4-nitrophenyl]methylcarbamoyl]methyl}carbamate dissolved in 150 ml of glacial acetic acid are treated with 23 g of stannous chloride and 30 ml of a mixture of concentrated hydrochloric acid and water (1:1). The mixture is stirred at room temperature for 20 hours, poured on to ice/ammonia and extracted several times with ethyl acetate. The organic solution is dried over sodium sulphate, filtered and concentrated. The residue is purified on a 350 g silica gel column using methylene chloride/ethyl acetate as the eluting agent and crystallised from methylene chloride/ether. There is obtained benzyl{[[4-amino-2-(o-fluorobenzoyl)-phenyl]methylcarbamoyl]methyl}carbamate which melts at 83° C.

(d) 0.8 g (0.0018 M) of benzyl{[[4-amino-2-(o-fluorobenzoyl)phenyl]methylcarbamoyl]methyl}carbamate dissolved in 10 ml of absolute tetrahydrofuran are treated with 0.2 ml of chloroethylisocyanate and the mixture is then stirred at room temperature for 24 hours. The mixture is treated with a further 0.1 ml of chloroethylisocyanate and stirred for 12 hours. The mixture is then concentrated and the residue is purified on a 70 g silica gel column using 5% ethyl acetate in methylene chloride as the eluting agent. The resulting benzyl{[[2-(o-fluorobenzoyl)-4-[3-(2-chloroethyl)ureido]phenyl]methylcarbamoyl]methyl}carbamate is further processed without isolation.

(e) 0.7 g of crude benzyl{[[2-(o-fluorobenzoyl)-4-[3-(2-chloroethyl)ureido]phenyl]methylcarbamoyl]methyl}carbamate dissolved in 15 ml of acetonitrile is treated with 400 mg of potassium acetate and 700 mg of 18-crown-6 and stirred at room temperature for 5 days. The mixture is then concentrated, the residue is treated with water/methylene chloride and the aqueous solution is extracted several times with methylene chloride. The organic solution is dried with sodium sulphate, filtered and concentrated. The residue is purified on a 30 g silica gel column using methylene chloride/ethyl acetate (3:1) as the eluting agent. The resulting benzyl{[[2-(o-fluorobenzoyl)-4-[3-(2-acetoxyethyl)ureido]-phenyl]methylcarbamoyl]methyl}carbamate is further processed without isolation.

(f) 250 mg of benzyl{[[2-(o-fluorobenzoyl)-4-[3-(2-acetoxyethyl)ureido]phenyl]methylcarbamoyl]methyl}carbamate dissolved in 10 ml of absolute methanol are treated with 50 mg of sodium methylate, stirred at room temperature for 1 hour and buffered with a small amount of acetic acid. The mixture is poured on to ice/10% sodium bicarbonate and extracted with methylene chloride. The organic solution is dried over sodium sulphate, filtered and concentrated. After crystallisation from ether/ethanol, there is obtained benzyl{[[2-(o-fluorobenzoyl)-4-[3-(2-hydroxyethyl)ureido]phenyl]-methylcarbamoyl]methyl}carbamate which melts at 117°–120 C.

(g) 200 mg (0.0004 M) of benzyl{[[2-(o-fluorobenzoyl)-4-[3-(2-hydroxyethyl)ureido]phenyl]methylcarbamoyl]methyl}carbamate are dissolved in 20 ml of ethanol, 20 mg of 5% palladium/active carbon are added thereto and the mixture is hydrogenated with hydrogen at room temperature and normal pressure. After 5 hours, the catalyst is filtered off, washed with methylene chloride and the solution is concentrated. The residue is crystallised from acetone. There is obtained 1-[5-(o-fluorophenyl)-2,3-dihydro-1-methyl-2-oxo-1H-1,4-benzodiazepin-7-yl]-3-(2-hydroxyethyl)-urea which melts at 156°–160° C. with decomposition. The N-hydroxyethyl-N'-[3-(o-fluorobenzoyl) (4-glycylamino)phenyl]urea which is formed as the intermediate is not isolated, but cyclises spontaneously.

EXAMPLE 38

(a) 1 g (0.0023 M) of benzyl{[[4-amino-2-(o-fluorobenzoyl)phenyl]methylcarbamoyl]methyl}carbamate dissolved in 100 ml of 1,2-dichloroethane is treated with 320 mg of powdered potassium carbonate and 0.25 ml of dimethylcarbamoyl chloride. The mixture is heated at reflux for 60 hours, cooled, treated with water and extracted three times with methylene chloride. The organic solution is washed once with water, dried with sodium sulphate and concentrated. The residue is purified on a 200 g silica gel column using ethyl acetate as the eluting agent and is then concentrated up to constant weight in a high vacuum. The thus-obtained oily benzyl{[[2-(o-fluorobenzoyl)-4-[3-(2-dimethyl)ureido]-phenyl]methylcarbamoyl]methyl}carbamate is further processed without isolation.

(b) 0.8 g of benzyl{[[2-(o-fluorobenzoyl)-4-[3-(2-dimethyl)ureido]phenyl]methylcarbamoyl]methyl}carbamate is dissolved in 5 ml of 30–33% hydrogen bromide solution in glacial acetic acid, stirred at room temperature for 15 minutes, treated with 10% sodium bicarbonate solution and extracted three times with methylene chloride. The methylene chloride extracts are dried over magnesium sulphate, filtered and concentrated. A portion of the residue is purified on a silica gel preparative plate using ethyl acetate/acetone as the eluting agent. According to the IR spectrum the thus-obtained product is identical with the 3-[5-(o-fluorophenyl)-2,3-dihydro-1-methyl-2-oxo-1H,-1,4-benzodiazepin-7-yl]-1,1-dimethylurea prepared in another manner (see Example 32).

EXAMPLE 39

(a) 2 g (0.0057 M) of N-[5-(o-fluorophenyl)-2,3-dihydro-1-methyl-2-oxo-1H-1,4-benzodiazepin-7-yl]-1-aziridinecarboxamide in 50 ml of tert.butanol are treated with 3 ml of 25% sulphuric acid. After 20 minutes, the mixture is made alkaline with 10% sodium bicarbonate solution and extracted several times with methylene chloride. The methylene chloride solution is dried over sodium sulphate, filtered and concentrated. The residue is purified on a 80 g silica gel column using ethyl acetate as the eluting agent and recrystallised from ethyl acetate. There is obtained 1-(2-tert.butoxyethyl)-3-[5-(o-fluorophenyl)-2,3-dihydro-1-methyl-2-oxo-1H-1,4-benzodiazepin-7-yl]urea which melts at 177° C.

(b) 50 mg (0.12 mM) of 1-(2-tert.butoxyethyl)-3-[5-(o-fluorophenyl)-2,3-dihydro-1-methyl-2-oxo-1H-1,4-benzodiazepin-7-yl]urea are dissolved in 1 ml of trifluoroacetic acid, the solution is left to stand at room temperature for 2 hours and then concentrated. The residue is taken up in 10% sodium bicarbonate solution and extracted several times with methylene chloride and a very small amount of methanol. The organic solution is dried over sodium sulphate, filtered and concentrated. The residue is crystallised from acetone/ether. According to the IR spectrum the product obtained is identical with the 1-[5-(o-fluorophenyl)-2,3-dihydro-1-methyl-2-oxo-1H-1,4-benzodiazepin-7-yl]-3-(2-hydroxyethyl)urea prepared in another manner (see Example 7).

EXAMPLE 40

A solution of 1 g (0.0028 M) of N-[5-(o-fluorophenyl)-2,3-dihydro-1-methyl-2-oxo-1H-1,4-benzodiazepin-7-yl]-1-aziridinecarboxamide in 50 ml of dioxan is acidified with a few drops of 25% sulphuric acid, made basic with ammonia after 20 minutes and extracted several times with methylene chloride and a very small amount of methanol. The organic solution is dried over sodium sulphate and filtered. The residue is purified on a 80 g silica gel column using acetone as the eluting agent and crystallised from acetone/ether. According to the IR spectrum, mixed melting point and melting point the isolated product is identical with the 1-[5-(o-fluorophenyl)-2,3-dihydro-1-methyl-2-oxo-1H-1,4-benzodiazepin-7-yl]-3-(2-hydroxyethyl)urea prepared in another manner (see Example 7).

EXAMPLE 41

(a) 4.2 g (0.015 M) of 7-amino-5-(o-fluorophenyl)-1,3-dihydro-1-methyl-2H-1,4-benzodiazepin-2-one are heated at reflux for 3 hours in 80 ml of absolute tetrahydrofuran with 3.5 ml of chloroethylisocyanate and a catalytic amount of triethylamine. The mixture is left to stand at room temperature overnight. The solution is concentrated on a steam-bath and the residue is crystallised from ethyl acetate. There is obtained 1-(2-chloroethyl)-3-[5-(o-fluorophenyl)-2,3-dihydro-1-methyl-2-oxo-1H-1,4-benzodiazepin-7-yl]urea which melts at 240° C. with decomposition.

(b) 760 mg (1.95 mM) of 1-(2-chloroethyl)-3-[5-(o-fluorophenyl)-2,3-dihydro-1-methyl-2-oxo-1H-1,4-benzodiazepin-7-yl]urea dissolved in 15 ml of acetonitrile are treated with 200 mg of potassium acetate and 520 mg of 18-crown-6. The mixture is then stirred at room temperature for 5 days, concentrated, treated with water/methylene chloride and the aqueous solution is extracted several times with methylene chloride. The organic solution is dried with sodium sulphate, filtered and concentrated. The residue is purified on a 70 g silica gel column using ethyl acetate as the eluting agent and crystallised from ethyl acetate/ether. According to the melting point and mixed melting point the isolated product is identical with the 2-[3-[5-(o-fluorophenyl)-2,3-dihydro-1-methyl-2-oxo-1H-1,4-benzodiazepin-7-yl]ureido]ethyl acetate prepared in another manner (see Example 36).

EXAMPLE 42

300 mg (0.73 mM) of 2-[3-[5-(o-fluorophenyl)-2,3-dihydro-1-methyl-2-oxo-1H-1,4-benzodiazepin-7-yl]ureido]ethyl acetate dissolved in 20 ml of absolute methanol are treated with 500 mg of sodium methylate and stirred at room temperature for 1 hour. The mixture is then buffered with a small amount of acetic acid and concentrated. The residue is treated with methylene chloride/10% sodium bicarbonate solution, the aqueous solution is extracted several times with methylene chloride and the organic solution is dried over sodium sulphate, filtered and concentrated. After crystallisation from acetone, there is obtained 1-[5-(o-fluorophenyl)-2,3-dihydro-1-methyl-2-oxo-1H-1,4-benzodiazepin-7-yl]-3-(2-hydroxyethyl)urea which according to the IR spectrum is identical with a sample of this substance prepared in another manner (see Example 7).

EXAMPLE 43

(a) 5 g (0.016 M) of 7-amino-6-chloro-5-(o-fluorophenyl)-1,3-dihydro-1-methyl-2H-1,4-benzodiazepin-2-one in 85 ml of absolute tetrahydrofuran are treated with 11.1 ml of chloroethylisocyanate and 1 ml of triethylamine. The mixture is stirred at room temperature for 1 week and heated at reflux for 5 hours. The mixture is treated with 50 ml of ethanol and concentrated. The residue is treated with methylene chloride/water and extracted several times with methylene chloride. The organic phase is separated, dried with sodium sulphate, filtered and concentrated. The residue is purified on a 300 g silica gel column using methylene chloride/ethyl acetate (3:1) as the eluting agent, there being obtained 1-(2-chloroethyl)-3-[6-chloro-5-(o-fluorophenyl)-2,3-dihydro-1-methyl-2-oxo-1H-1,4-benzodiazepin-7-yl]urea which is further processed directly.

(b) 3.7 g of 1-(2-chloroethyl)-3-[6-chloro-5-(o-fluorophenyl)-2,3-dihydro-1-methyl-2-oxo-1H-1,4-benzodiazepin-7-yl]urea dissolved in 100 ml of acetonitrile are treated with 1.83 g of potassium acetate and 4.21 g of 18-crown-6. The mixture is then stirred at room temperature for 5 days, concentrated, treated with water/methylene chloride and the aqueous solution is extracted several times with methylene chloride. The organic solution is dried with sodium sulphate, filtered and concentrated. The residue is purified on a 350 g silica gel column using ethyl acetate as the eluting agent and crystallised from ethanol/ether. There is obtained 2-[3-[6-chloro-5-(o-fluorophenyl)-2,3-dihydro-1-methyl-2-oxo-1H-1,4-benzodiazepin-7-yl]ureido]ethyl acetate.

EXAMPLE 44

600 mg of 2-[3-[6-chloro-5-(o-fluorophenyl)-2,3-dihydro-1-methyl-2-oxo-1H-1,4-benzodiazepin-7-yl]ureido]ethyl acetate dissolved in 35 ml of absolute methanol are treated with 830 mg of sodium methylate and stirred at room temperature for 1 hour. The mixture is buffered with a small amount of acetic acid and concentrated. The residue is treated with methylene chloride/10% sodium bicarbonate solution, the aqueous solution is extracted with methylene chloride and the organic solution is dried over sodium sulphate, filtered and concentrated. The residue is purified on a 30 g silica gel column with ethyl acetate/methanol (10:1) as the eluting agent and crystallised from ethanol/ether.

There is obtained 1-[6-chloro-5-(o-fluorophenyl)-2,3-dihydro-1-methyl-2-oxo-1H-1,4-benzodiazepin-7-yl]-3-(2-hydroxyethyl)urea which, according to the melting point, mixed melting point and IR spectrum, is identical with a sample prepared in another manner (see Example 13).

EXAMPLE 45

100 mg (0.26 mM) of 1-(2-chloroethyl)-3-[5-(o-fluorophenyl)-2,3-dihydro-1-methyl-2-oxo-1H-1,4-benzodiazepin-7-yl]urea are stirred in 6 ml of benzene and 4 ml of water with 150 mg of tetrabutylammonium bromide for 16 hours at 80° C. The mixture is then concentrated and the residue is chromatographed in a pressure column (0.2–0.4 atmospheres of nitrogen) on 15 g of silica gel (particle size 0.04–0.063 mm) using ethyl acetate and ethyl acetate containing 3% methanol as the eluting agent, there being obtained a crude product containing 1-[5-(o-fluorophenyl)-2,3-dihydro-1-methyl-2-oxo-1H-1,4-benzodiazepin-7-yl]-3-(2-hydroxyethyl)urea and polar impurities.

This crude product (60 mg) is taken up in methylene chloride/water, extracted and the methylene chloride solution is dried over sodium sulphate, filtered and concentrated.

The residue is chromatographed in a pressure column (0.2–0.4 atmospheres of nitrogen) on 15 g of silica gel (particle size 0.04–0.063 mm) using absolute acetone as the eluting agent and crystallised from acetone/ether. According to the IR spectrum, the product obtained is identical with a sample of 1-[5-(o-fluorophenyl)-2,3-dihydro-1-methyl-2-oxo-1H-1,4-benzodiazepin-7-yl]-3-(2-hydroxyethyl)urea prepared in another manner (see Example 7).

EXAMPLE 46

(a) A dichloroethane solution of [5-(o-fluorophenyl)-2,3-dihydro-1-methyl-2-oxo-1H-1,4-benzodiazepin-7-yl]isocyanate, obtained as described in paragraph (a) of Example 1 from 10.4 g (0.037 M) of 7-amino-5-(o-fluorophenyl)-1,3-dihydro-1-methyl-2H-1,4-benzodiazepin-2-one, is treated with 9.1 g (0.044 M) of N-benzyl-O-tert.butyl-ethanolamine in 90 ml of dichloroethane. The organic phase is washed twice with water, dried over sodium sulphate, filtered and concentrated. The residue is purified on a 600 g silica gel column using ethyl acetate as the eluting agent and crystallised from methylene chloride/n-hexane. There is obtained 1-benzyl-1-(2-tert.butoxyethyl)-3-[5-(o-fluorophenyl)-2,3-dihydro-1-methyl-2-oxo-1H-1,4-benzodiazepin-7-yl]urea which melts at 82°–86° C.

(b) 200 mg (0.4 mM) of 1-benzyl-1-(2-tert.butoxyethyl)-3-[5-(o-fluorophenyl)-2,3-dihydro-1-methyl-2-oxo-1H-1,4-benzodiazepin-7-yl]urea are heated on a steam-bath for 10 minutes in 3 ml of a 33% solution of hydrogen bromide in glacial acetic acid and then left to stand at room temperature for 3 days. The mixture is neutralised with sodium bicarbonate and extracted several times with methylene chloride. The methylene chloride extracts are combined, dried over sodium sulphate, filtered and concentrated. The residue is purified in a pressure column (0.2–0.4 atmospheres of nitrogen) on 15 g of silica gel (particle size 0.04–0.06 mm) using ethyl acetate as the eluting agent and crystallised from ethyl acetate/ether, there being obtained 2-[3-[5-(o-fluorophenyl)-2,3-dihydro-1-methyl-2-oxo-1H-1,4-benzodiazepin-7yl]ureido]ethyl acetate which melts at 196°–198° C.

(c) 20 mg (0.048 mM) of 2-[3-[5-(o-fluorophenyl)-2,3-dihydro-1-methyl-2-oxo-1H-1,4-benzodiazepin-7-yl]ureido]ethyl acetate are dissolved in 2 ml of absolute methanol and stirred at 30°–40° C. for 1 hour with 13 mg of sodium methylate. The mixture is then buffered with a few drops of glacial acetic acid, diluted with methylene chloride, treated with 10% sodium bicarbonate solution and extracted several times with methylene chloride. The organic phases are combined, dried over sodium sulphate, filtered and concentrated. The residue is crystallised from acetone/ether. There is obtained 1-[5-(o-fluorophenyl)-2,3dihydro-1-methyl-2-oxo-1H-1,4-benzodiazepin-7-yl]-3-(2-hydroxyethyl)urea which, according to the IR spectrum, is identical with a sample of this substance prepared in another manner (see Example 7).

EXAMPLE 47

1.5 g (0.003 M) of 1-benzyl-1-(2-tert.butoxyethyl)-3-[5-(o-fluorophenyl)-2,3-dihydro-1-methyl-2-oxo-1H-1,4-benzodiazepin-7-yl]urea are dissolved in 15 ml of 48% aqueous hydrogen bromide solution, the mixture is heated on a steam-bath for 10 minutes, made alkaline with sodium bicarbonate, treated with a small amount of methanol and extracted three times with methylene chloride. The extracts are combined, dried over sodium sulphate, filtered and concentrated. The residue is purified in a pressure column (0.2–0.4 atmosphere of nitrogen) on 300 g of silica gel (particle size 0.04–0.06 mm) using acetone as the eluting agent and crystallised from acetone/ether. There is obtained 1-[5-(o-fluorophenyl)-2,3-dihydro-1-methyl-2-oxo-1H-1,4-benzodiazepin-7-yl]-3-(2-hydroxyethyl)urea which, according to the IR spectrum, is identical with a sample of this substance prepared in another manner (see Example 7).

EXAMPLE 48

(a) From 40 g (0.116 M) of rac-5-(o-chlorophenyl)-1,3-dihydro-1,3-dimethyl-7-nitro-2H-1,4-benzodiazepin-2-one there is obtained in analogy to the procedure described in paragraph (d) of Example 31 rac-7-amino-5-(o-chlorophenyl)-1,3-dihydro-1,3-dimethyl-2H-1,4-benzodiazepin-2-one which is crystallised from ethyl acetate/petroleum ether and melts at 180°–190° C.

(b) From 4.7 g (0.015 M) of rac-7-amino-5-(o-chlorophenyl)-1,3-dihydro-1,3-dimethyl-2H-1,4-benzodiazepin-2-one there is obtained in analogy to the procedure described in paragraph (e) of Example 31 rac-7-amino-6-bromo-5-(o-chlorophenyl)-1,3-dihydro-1,3-dimethyl-2H-1,4-benzodiazepin-2-one which is crystallised from ethyl acetate/ether and melts at 254°–256° C. with decomposition.

(c) From 3 g (0.0076 M) of rac-7-amino-6-bromo-5-(o-chlorophenyl)-1,3-dihydro-1,3-dimethyl-2H-1,4-benzodiazepin-2-one there is obtained in analogy to the procedure described in paragraph (f) of Example 31 rac-1-[6-bromo-5-(o-chlorophenyl)-2,3-dihydro-1,3-dimethyl-2-oxo-2H-1,4-benzodiazepin-7-yl]-3-(2-hydroxyethyl)urea which is crystallised from acetone/ether and melts at 204°–206° C. with decomposition.

EXAMPLE 49

(a) From 15 g (0.045 M) of rac-7-amino-5-(o-chlorophenyl)-1,3-dihydro-1,3-dimethyl-2H-1,4-benzodiazepin-2-one there is obtained in analogy to the procedure described in paragraph (a) of Example 29 rac-7-amino-6-chloro-5-(o-chlorophenyl)-1,3-dihydro-1,3-dimethyl-2H-1,4-benzodiazepin-2-one which is crystallised from ethyl acetate and melts at 240°–242° C. with decomposition.

(b) From 7 g (0.02 M) of rac-7-amino-6-chloro-5-(o-chlorophenyl)-1,3-dihydro-1,3-dimethyl-2H-1,4-benzodiazepin-2-one there is obtained in analogy to the procedure described in paragraph (b) of Example 29 rac-1-[6-chloro-5-(o-chlorophenyl)-2,3-dihydro-1,3-dimethyl-2-oxo-1H-1,4-benzodiazepin-7-yl]-3-(2-hydroxyethyl)urea which is crystallised from acetone and melts at 233°–236° C. with decomposition.

EXAMPLE 50

(a) From 15 g (0.05 M) of 7-amino-5-(o-fluorophenyl)-1,3-dihydro-1,3-dimethyl-2H-1,4-benzodiazepin-2-one there is obtained in analogy to the procedure described in paragraph (e) of Example 31 rac-7-amino-6-bromo-5-(o-fluorophenyl)-1,3-dihydro-1,3-dimethyl-2H-1,4-benzodiazepin-2-one which is crystallised from ethyl acetate/ether and melts at 255° C. with decomposition.

(b) From 4.4 g (0.012 M) of rac-7-amino-6-bromo-5-(o-fluorophenyl)-1,3-dihydro-1,3-dimethyl-2H-1,4-benzodiazepin-2-one there is obtained in analogy to the procedure described in paragraph (f) of Example 31 rac-1-[6-bromo-5-(o-fluorophenyl)-2,3-dihydro-1,3-dimethyl-2-oxo-1H-1,4-benzodiazepin-7-yl]-3-(2-hydroxyethyl)urea which is crystallised from acetone/ether and melts at 210°–212° C:

EXAMPLE 51

From 6 g (0.019 M) of 7-amino-6-chloro-5-(o-fluorophenyl)-1,3-dihydro-1-methyl-2H-1,4-benzodiazepin-2-one there is obtained in analogy to the procedure described in Example 17 but using morpholine instead of N-methylpiperazine N-[6-chloro-5-(o-fluorophenyl)-2,3-dihydro-1-methyl-2-oxo-1H-1,4-benzodiazepin-7-yl]-4-morpholinecarboxamide which is crystallised from ethyl acetate/ether and melts at 126° C.

The following Example illustrates pharmaceutical preparations containing benzodiazepine derivatives provided by the present invention:

EXAMPLE A

1-[5-(o-Fluorophenyl)-2,3-dihydro-1-methyl-2-oxo-1H-1,4-benzodiazepin-7-yl]-3-(2-hydroxyethyl)urea can be used as follows as the active ingredient for the manufacture of pharmaceutical preparations:

| (a) | Tablets | Per Tablet |
|---|---|---|
| | Active ingredient | 200 mg |
| | Microcrystalline cellulose | 155 mg |
| | Maize starch | 25 mg |
| | Talc | 25 mg |
| | Hydroxypropylmethylcellulose | 20 mg |

| (a) | Tablets | Per Tablet |
|---|---|---|
| | -continued | |
| | | 425 mg |

The active ingredient is mixed with half of the microcrystalline cellulose and granulated with a 10% solution of hydroxypropylmethylcellulose in a mixture of isopropanol and methylene chloride. The granulate is dried, sieved and mixed with the remainder of the adjuvants. The resulting mixture is pressed on a press to biplanar tablets having a diameter of 12 mm and a break-bar.

| (b) | Capsules | Per Capsule |
|---|---|---|
| | Active ingredient | 100.0 mg |
| | Maize starch | 20.0 mg |
| | Lactose | 95.0 mg |
| | Talc | 4.5 mg |
| | Magnesium stearate | 0.5 mg |
| | | 220.0 mg |

The active ingredient is mixed with the adjuvants and sieved. After mixing again, the capsule fill mass obtained is filled into interlocking gelatin capsules of suitable size on a completely automatic capsule filling machine.

What is claimed:

1. Compounds of the general formula

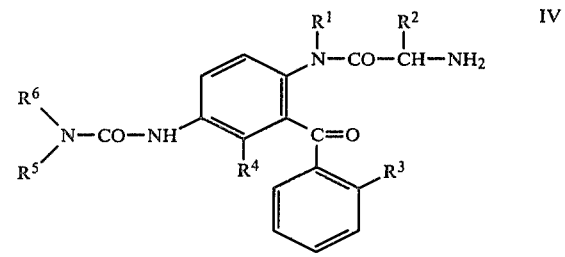

wherein $R^1$ represents a lower alkyl group, $R^2$ represents a hydrogen atom or a lower alkyl group, $R^3$ represents a halogen atom and $R^4$ represents a hydrogen or halogen atom and either $R^5$ represents a hydrogen atom or a lower alkyl group and $R^6$ represents a lower alkyl, lower hydroxyalkyl or lower acyloxyalkyl group or $R^5$ represents a hydrogen atom and $R^6$ represents an aryl or lower aralkyl group or $R^5$ and $R^6$ together with the nitrogen atom to which they are attached represent a 3-membered to 7-membered heterocycle which, when it is at least 5-membered, can contain as a ring member an oxygen or sulphur atom or a group of the formula $>N-R^7$ in which $R^7$ represents a hydrogen atom or a lower alkyl group.

2. N-Hydroxyethyl-N'-[(3-o-fluorobenzoyl)(4-glycylamino)phenyl]urea.

* * * * *